(12) United States Patent
Narang et al.

(10) Patent No.: US 10,228,358 B2
(45) Date of Patent: Mar. 12, 2019

(54) APPARATUS AND METHOD FOR THE ASSESSMENT OF CONCENTRATION PROFILING AND PERMEABILITY RATES

(71) Applicant: Pion Inc., Billerica, MA (US)

(72) Inventors: Ajit S. Narang, Monmouth Junction, NJ (US); Dan Tang, Brooklyn, NY (US); Scott P. Jennings, Bridgewater, NJ (US); Neil Mathias, North Brunswick, NJ (US); Konstantin L. Tsinman, Littleton, MA (US); Deren J. Dohoda, Billerica, MA (US); David A. Kwajewski, Wilbraham, MA (US); Michael G. Kelly, Waltham, MA (US)

(73) Assignee: PION INC., Billerica, MA (US)

( * ) Notice: Subject to any disclaimer, the term of this patent is extended or adjusted under 35 U.S.C. 154(b) by 0 days.

(21) Appl. No.: 15/098,514

(22) Filed: Apr. 14, 2016

(65) Prior Publication Data

US 2016/0305922 A1 Oct. 20, 2016

Related U.S. Application Data

(60) Provisional application No. 62/148,879, filed on Apr. 17, 2015.

(51) Int. Cl.
*G01N 33/15* (2006.01)
*G01N 13/00* (2006.01)
(Continued)

(52) U.S. Cl.
CPC ............ *G01N 33/15* (2013.01); *G01N 13/00* (2013.01); *G01N 15/08* (2013.01);
(Continued)

(58) Field of Classification Search
None
See application file for complete search history.

(56) References Cited

U.S. PATENT DOCUMENTS

| 4,335,438 A | 6/1982 | Smolen |
| 4,468,951 A | 9/1984 | Garcia et al. |

(Continued)

FOREIGN PATENT DOCUMENTS

| EP | 2182342 A1 | 5/2010 |
| WO | 2005/095950 A1 | 10/2005 |

(Continued)

OTHER PUBLICATIONS

Avdeef, A. et al., "PAMPA—A Drug Absorption In Vitro Model. 13. Chemical Selectivity Due to Membrane Hydrogen Bonding: In Combo Comparisons of HDM-, DOPC-, and DS-PAMPA Models," Eur. J. Pharm Sci., vol. 28(1), pp. 43-50 (2006). Eight pages.
Borbas, E. et al., "Investigation and Mathematical Description of the Real Driving Force of Passive Transport of Drug Molecules from Supersaturated Solutions," Molecular Pharmaceutics, pp. A-K (Web Publication: Sep. 9, 2016). Eleven pages.

(Continued)

*Primary Examiner* — Paul S Hyun
(74) *Attorney, Agent, or Firm* — HoustonHogle LLP; Anabela Taylor

(57) ABSTRACT

An apparatus for the combined assessment of dissolution and permeability relies on a receiver chamber that is contained within a donor chamber. A membrane is provided between the two chambers. Measurements can be taken to determine solute amounts of a drug introduced in the donor chamber and amounts of permeated solute in the receiver chamber. Also described are techniques for the assessment of a dissolution rate and total amount of dissolved compound, together with their effect on absorption potential of a compound or a compound product as well as approaches for evaluating in vivo relevant differences between formulations of a compound through their effect on the absorption potential of the compound.

17 Claims, 20 Drawing Sheets

(51) Int. Cl.
*G01N 15/08* (2006.01)
*G01N 15/00* (2006.01)

(52) U.S. Cl.
CPC ............ *G01N 2013/006* (2013.01); *G01N 2015/0065* (2013.01); *G01N 2015/086* (2013.01)

(56) References Cited

U.S. PATENT DOCUMENTS

| | | | |
|---|---|---|---|
| 5,032,524 | A | 7/1991 | Büntemeyer et al. |
| 5,412,979 | A | 5/1995 | Fassihi |
| 5,827,984 | A | 10/1998 | Sinnreich et al. |
| 6,004,822 | A | 12/1999 | Li et al. |
| 6,022,733 | A | 2/2000 | Tam et al. |
| 6,060,024 | A | 5/2000 | Hutchins et al. |
| 6,174,497 | B1 | 1/2001 | Roinestad et al. |
| 6,521,191 | B1 | 2/2003 | Schenk et al. |
| 6,558,957 | B1 | 5/2003 | Roinestad et al. |
| 6,929,782 | B1 | 8/2005 | Ciliberto et al. |
| 7,022,528 | B2 | 4/2006 | Avdeef et al. |
| 7,024,955 | B2 | 4/2006 | Carlson et al. |
| 7,094,341 | B2 | 8/2006 | Max |
| 7,147,826 | B2 | 12/2006 | Haywood et al. |
| 7,237,436 | B2 | 7/2007 | Tian et al. |
| 7,611,630 | B2 | 11/2009 | Babcock et al. |
| 7,767,463 | B2 | 8/2010 | Quinn et al. |
| 8,133,721 | B2 | 3/2012 | Yang et al. |
| 8,158,059 | B2 | 4/2012 | Kennedy et al. |
| 8,163,537 | B2 | 4/2012 | Martin et al. |
| 8,175,815 | B2 | 5/2012 | Avdeef et al. |
| 8,518,327 | B2 | 8/2013 | Kennedy et al. |
| 8,584,539 | B2 | 11/2013 | Wright et al. |
| 9,546,991 | B2 | 1/2017 | Li et al. |
| 2004/0087005 | A1 | 5/2004 | Henderson et al. |
| 2005/0176155 | A1 | 8/2005 | Klein et al. |
| 2007/0160497 | A1 | 7/2007 | Hughes et al. |
| 2007/0298451 | A1 | 12/2007 | Ribault et al. |

FOREIGN PATENT DOCUMENTS

| | | | |
|---|---|---|---|
| WO | 2008/112245 A1 | 9/2008 | |
| WO | WO-2014053840 A1 * | 4/2014 | ............ G01N 33/50 |

OTHER PUBLICATIONS

Borbas, E. et al., "In Vitro Dissolution-Permeation Evaluation of an Electrospun Cyclodextrin-Based Formulation of Aripiprazole Using μFLUX(TM)," International Journal of Pharmaceutics, vol. 491, pp. 180-189 (2015).

Ginski, M. et al., "Prediction of Dissolution-Absorption Relationships from a Continuous Dissolution/Caco-2 System," AAPS Pharmsci, vol. 1(3) article 3, (1999). http://www.pharmsci.org. Twelve pages.

Ginski, M. et al., "Prediction of dissolution-absorption relationships from a dissolution/Caco-2 system," International Journal of Pharmaceutics, vol. 177, pp. 117-125 (1999). Nine pages.

Kataoka, M. et al., "Application of Dissolution/Permeation System for Evaluation of Formulation Effect on Oral Absorption of Poorly Water-Soluble Drugs in Drug Development," Pharmaceutical Research, vol. 29, pp. 1485-1494 (2012). Ten pages.

Kataoka, M. et al., "In Vitro System to Evaluate Oral Absorption of Poorly Water-Soluble Drugs: Simultaneous Analysis on Dissolution and Permeation of Drugs," Pharmaceutical Research, vol. 20(10), pp. 1674-1680 (Oct. 2003). Seven pages.

Kobayashi, M. et al., "Development of a New System for Prediction of Drug Absorption That Takes Into Account Drug Dissolution and pH Change in the Gastro-Intestinal Tract," International Journal of Pharmaceutics, vol. 221, pp. 87-94 (2001). Eight pages.

Mudie, D.M. et al., "Mechanistic Analysis of Solute Transport in an In Vitro Physiological Two-Phase Dissolution Apparatus," Biopharm. Drug Dispos., vol. 33(7), pp. 378-402 (Oct. 2012). Thirty-eight pages.

Pion μFLUX(TM) "Enabling Real-Time Pharmacokinetic Decision Making," Brochure, AAPS, www.pion-inc.com. Oct. 2013. Two pages.

Pion MacroFLUX "Bringing dissolution closer to IVIVC than ever before!" Flyer, AAPS, www.pion-inc.com. Oct. 2015. One page.

Tsinman, K. et al., "An Integration of Absorption Chamber with USP II Dissolution Apparatus," Poster M1324 Presented at AAPS Meeting Oct. 26-29, 2015. One page.

International Search Report and Written Opinion, dated Jul. 7, 2016, for International Application No. PCT/US2016/027502, filed Apr. 14, 2016. Thirteen pages.

International Preliminary Report on Patentability, dated Jul. 6, 2017, from International Application No. PCT/US2016/027502, filed on Apr. 14, 2016. Ten pages.

* cited by examiner

APPARATUS AND METHOD FOR THE ASSESSMENT OF CONCENTRATION PROFILING AND PERMEABILITY RATES

RELATED APPLICATIONS

This application claims the benefit under 35 USC 119(e) of U.S. Provisional Application No. 62/148,879, filed on Apr. 17, 2015, which is incorporated herein by reference in its entirety.

BACKGROUND OF THE INVENTION

Solubility, dissolution and permeability are important factors in the screening, evaluation, production or administration of pharmaceutical compounds. The Biopharmaceutics Classification System (BCS), for example, uses these parameters to characterize drug substances into four groups. Highly permeable and highly soluble compounds (Class I) are well absorbed, with typical absorption rates higher than excretion. For high permeability, low solubility drugs (Class II) bioavailability is limited by the solubility and/or dissolution rate. Drugs that belong in Class III are characterized by low permeability and high solubility, typically exhibiting an absorption limited by the permeation rate. Low permeability, low solubility compounds (Class IV) tend to be poorly absorbed over the intestinal mucosa and often exhibit high variability in pharmaco-kinetic (PK) studies.

In many cases, solubility, dissolution and permeability of solid oral doses are studied individually. Dissolution (sometimes also referred to as "release") characteristics, for example, are routinely tested in vitro, in the preliminary stages of drug development, or to ensure batch to batch quality control during the manufacturing process. Techniques for correlating laboratory results to in vivo behavior as well as standardized equipment and protocols for dissolution testing have been developed. The United States Pharmacopeia (USP), for example, describes several systems, including USP Dissolution Apparatus I—Basket (37° C.) and USP Dissolution Apparatus II—Paddle (37° C.).

Laboratory methods for investigating permeability often rely on membranes that mimic in vivo systems. Human colon carcinoma epithelial cell line Caco-2 cell monolayers, for example, are routinely used as a model of the human small intestinal mucosa. Permeability across a membrane such as a Caco-2 cell monolayer can then be correlated to in vivo absorption according to suitable protocols.

A frequently used approach in permeability studies is the "parallel artificial membrane permeability assay" or PAMPA. In this approach, a compound is studied as it permeates from a donor compartment, through a lipid-infused filter support constituting artificial membrane into an acceptor compartment. In traditional PAMPA, a multi-well microtitre plate (hence "parallel") is used for the donor and a membrane/acceptor compartment is placed on top; the whole assembly is often referred to as a "sandwich". A PAMPA test is usually initiated by adding the pre-dissolved drug under investigation to the donor compartment, and providing a drug-free acceptor compartment. After an incubation period which may include stirring, in one or both compartments, the sandwich is separated and the amount of drug in each compartment may be measured. Drug amounts retained in the membrane can be determined using mass balance calculations or other techniques.

Though generally PAMPA cannot measure active permeability (a form of transport that uses cellular energy and relies on the movement of molecules across a cell membrane that not necessarily aligned with the concentration gradient, e.g., moving from a low concentration to a high concentration), PAMPA can provide valuable information regarding passive transport, i.e., a movement of atoms or molecules (e.g., biochemicals) across cell membranes that does not require an input of chemical energy but is driven by an increase in the entropy of the system. The rate of passive transport expressed by the permeability constant depends in part on the interaction between the permeating molecule and the barrier membrane, which, in turn, depends on the organization and characteristics of the membrane lipids and proteins.

In many cases, PAMPA is used in the early screenings of active pharmaceutical ingredients (API), while Caco-2 studies are used in later stages of drug development.

Several attempts to combine dissolution and permeability (typically using Caco-2 monolayers) assessments also have been undertaken. An article by M. J. Ginski et al., with the title *Prediction Of Dissolution-Absorption Relationships From A Continuous Dissolution/Caco-2 System*, AAPS Pharm Sci 1: E3 (1999), for instance, describes an arrangement in which a USP apparatus II (rotating paddle) is used as a dissolution vessel. The dissolution chamber is linked to a permeation chamber containing a donor compartment (cell) and a receiver (absorption) compartment (cell) in a side-by-side arrangement. A peristaltic pump is used to transfer medium from the dissolution vessel to the donor compartment and permeation occurs through a Caco-2 cell monolayer separating the two cells.

A more complex approach, proposed by M. Kobayashi et al., *Development Of A New System For Prediction Of Drug Absorption That Takes Into Account Drug Dissolution And pH Change In The Gastro-Intestinal Tract*, Int. J. Pharm. 221: 87-94 (2001), employs separate vessels for dissolution, pH adjustment and permeation.

Yet another arrangement is described by M. Kataoka et al. in the paper *In Vitro System To Evaluate Oral Absorption Of Poorly Water-Soluble Drugs: Simultaneous Analysis On Dissolution And Permeation Of Drugs*, Pharm. Res. 20: 1674-1680 (2003). The approach involves a downsized vessel containing a Caco-2 monolayer between an apical side and a basal side. The drug to be tested is introduced to the apical side and dissolution profiles are established by blocking the Caco-2 monolayer with a flat aluminum sheet. Permeation is measured by taking aliquots from the basal side.

Other designs rely on a single compartment, containing a layer of 1-octanol above a water layer, to simultaneously study the release and partitioning of a drug in the two phases.

SUMMARY OF THE INVENTION

Although approaches aimed at combining dissolution and permeability assessments described above present advantages over the separate evaluation of these parameters, many problems remain. In some cases, the design and use of combined dissolution/permeability arrangements is complicated by the two or more chambers required. Conduits and pumps introduce additional complexity to these systems. The possibility of uneven mixing during transfer between multiple (two or more) chambers and the failure to meet dissolution compendial requirements (e.g., for USP apparatus I or II) present further drawbacks. For higher throughput testing, valuable capacity is lost since the number of samples evaluated is only half the number of vessels required to run the test.

Difficulties also are encountered with the Kataoka et al. approach. The downsized setup, for example, requires commensurately small and thus difficult to handle drug amounts. Moreover, these reduced amounts fail to meet compendial dosage requirements.

Furthermore, dissolution studies alone often cannot predict what happens in vivo. For example, in some cases differences in the dissolution profile would potentially lead to the discarding of a production batch of the drug or abandoning a certain formulation while there could be no batch-to-batch variations on the absorption/bioavailability profile of the drug. In other cases, there would be no differences in the dissolution profiles between various batches or formulations of API while there could be significant variation in their in vivo performance.

A need exists, therefore, to address inadequacies associated with existing arrangements and techniques. In particular, a need exists for a simplified approach for the combined assessment of both dissolution and permeability properties and, preferably, an approach with the additional potential of meeting compendial requirements. A need also exists for improved predictability of in vivo behavior of a compound, e.g., a drug or formulation.

Thus in some of its aspects, the invention relates to a method or apparatus suitable for characterizing and/or predicting in vivo absorption potential of a compound, often an active ingredient or a product containing the compound, e.g., the active ingredient. Embodiments disclosed herein relate to measuring an in vitro absorption potential, a parameter that could be expressed, for example, in the form of flux through the permeation membrane (i.e. amount of compound or compound product penetrating through the membrane per unit area per unit time, e.g., in $mg*min^{-1}*cm^{-2}$ units); total amount of material (compound or compound product) permeated to the receiver compartment during a particular time period (e.g., in mg units); relative amount of compound or compound product permeated to the receiver compartment (e.g., in %); or another parameter that would directly or indirectly include in itself dependence on solubility of the compound or compound product, its dissolution or precipitation and its permeability.

In specific embodiments the invention relates to a method for evaluating the absorption potential of a compound (or compound product), using, for example, the assessment, and in many cases the combined assessment, of concentration profiling (e.g., dissolution rate or amount of compound present as a function of time), total amount of the compound (e.g. total amount of dissolved compound) and effects of these parameters on the absorption potential.

In one aspect, a method for assessing an absorption potential of a compound or compound product comprises: introducing the compound or the compound product into a first medium, typically a dissolution or donor medium; measuring the amount of dissolved compound or dissolved compound product in the first medium as a function of time to obtain a dissolution rate; measuring the amount of dissolved compound or dissolved compound product in a second medium, typically a receiving medium, as a function of time, to obtain an absorption potential parameter; and determining or evaluating whether a change or lack thereof in the dissolution rate and/or total amount of dissolved compound or compound product causes a change in the absorption potential parameter.

In another aspect, a method for assessing an absorption potential of a compound or a compound product includes: introducing the compound or the compound product into a first medium; measuring the amount of compound or compound product in the first medium as a function of time to obtain a concentration profile; measuring the amount of compound or compound product in a second medium as a function of time to obtain an absorption potential parameter; and determining or evaluating if a change or lack thereof in the concentration profile and/or total amount of compound or compound product causes a change in the absorption potential parameter.

Typically, the first and second media are separated by a permeation membrane. In specific implementations, the absorption potential parameter is a flux through the membrane, a total or relative amount of material collected in the receiving medium over a selected period of time, an area under a concentration-time profile in the receiving medium or another parameter indicative of the solubility of the compound or compound product, dissolution or precipitation rate of the compound or compound product and permeability of the compound or compound product.

In a further aspect, the invention relates to method for evaluating absorption or in vivo relevant differences, between formulations of a compound through effects of said differences on absorption potential of the compound. The method includes: introducing a first formulation of the compound into a dissolution medium; determining (if possible) the amount of dissolved compound in the dissolution medium as a function of time; determining the amount of dissolved compound in a receiving medium as a function of time; assessing absorption, or in vivo relevant changes in dissolution rate, by comparing an absorption potential parameter or characteristic of the compound or formulation, for example, flux through a membrane separating the dissolution and receiving media, with a reference absorption potential, for instance, the absorption potential of the neat compound or the absorption potential of a different formulation of the compound or compound product.

In a further aspect, the invention relates to a method for the combined assessment of dissolution and permeation rates of an ingredient. The method includes: introducing a sample into a dissolution medium to obtain a solute ingredient, allowing the solute ingredient to permeate to a receiving medium; and measuring the concentration of the solute ingredient in the dissolution medium and in the receiving medium, wherein the receiving medium is contained in a vessel that is partially or completely immersed in the dissolution medium.

Other embodiments of the invention relate to an apparatus for measuring dissolution and permeability. The apparatus includes: a receiving vessel having a membrane permeable to a solute, wherein the receiving chamber is partially or completely immersed in a dissolution vessel; a stirring device disposed in the dissolution vessel; and an optional stirring device in the receiving vessel. The apparatus can further include a first device, also referred to herein as "probe", for measuring a solute concentration in the dissolution vessel; and/or a second device for measuring a solute concentration in the receiving vessel.

The apparatus or components thereof can be configured to meet compendial requirements and/or can be part of a kit.

Practicing embodiments described herein can have many advantages. For example, information regarding both dissolution and permeability properties of a compound can be obtained in a single apparatus, in a rapid and simplified approach compared to techniques that study these properties individually. Embodiments described herein can be used in pre-formulation and formulation development, e.g., selection of excipient, carriers, additives and/or other ingredients that improve absorption properties of API, providing data for in vitro-in vivo correlations (IVIVC), quality control/quality assurance, e.g., during FDA application and approval procedures, in the manufacturing process, analytical work or other situations. Techniques presented herein can be employed to study or screen existing formulations (e.g., brand names versus generic) or formulations being developed, with the goal, for instance, of arriving at a desired dissolution-permeation behavior.

Compared to designs that utilize existing compendial configurations and connect two neighboring vessels, the relatively small volume of the receiver chamber increases the sensitivity in the receiver due to an increase of area-to-volume ratio. Unstirred connector volumes are eliminated, thus enhancing mixing uniformity and reproducibility in the dissolution and in the receiver vessels. While in typical units with neighboring side by side vessels the number of collected replicates is only half the total number of vessels, the nested design described herein allows for twice as many replicates.

Advantageously, the present apparatus can be configured to fit at the sampling location of a standard 900 mL dissolution vessel. It can also be configured to fit 500 mL or 250 mL setups, in particular in designs in which the receiver assembly is immersed from above. The apparatus described herein also can be configured to fit into an existing dissolution unit regardless of the dissolution unit design, e.g., whether bathless or not, specific location of vessels and so forth. As such, the present apparatus can be independent from a particular bath design or manufacturer and thus more easily adaptable and readily accepted in standardized protocols.

Compendial and other standard dissolution approaches can display variability in dissolution profiles, including declining dissolution rates. The biorelevance of this variability is not well understood, in spite of the criticality of this drug product quality. It is believed that embodiments described herein can provide biorelevant context to declining dissolution that can be used in conjunction with biopharmaceutic modeling and simulations and other modeling techniques.

The above and other features of the invention including various details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Large numbers of compounds are tested routinely to determine potential pharmaceutical benefits. Those that exhibit a desired activity are further tested for indicators of in vivo absorption. Only a handful of promising candidates reach the drug development phase and even fewer enter scaled-up production and the market.

The embodiments described herein relate to an apparatus and method for the combined assessment of dissolution and permeability properties of a compound or a product containing the compound. Compounds that can be studied include but are not limited to pharmaceutical or biopharmaceutical substances, veterinary substances, dietary supplements, recreational drugs, toxic or hazardous compounds, and many others. The compound can be a component in a combination or mixture referred to herein as a "compound product" or "product", such as, for example a formulation that contains (pharmaceutically) active and/or inactive materials. In specific embodiments, the present apparatus and method are used during initial screenings for active ingredient products (API), during the development stage, approval process (e.g., for quality control (QC) and/or quality assurance (QA)) and/or during manufacturing. Agricultural products, toxicity assessments, chemical analysis, and other fields also can employ configurations and techniques described herein.

Generally, the apparatus described herein includes a donor vessel, a receiver vessel and a membrane suitable to evaluate permeability of a compound. In contrast to arrangements having side by side (or neighboring) containers (illustrated in FIG. 1), many embodiments of the present apparatus and method utilize a system in which one vessel is partially or entirely contained in the other, e.g., in a nested arrangement.

Figure 1:
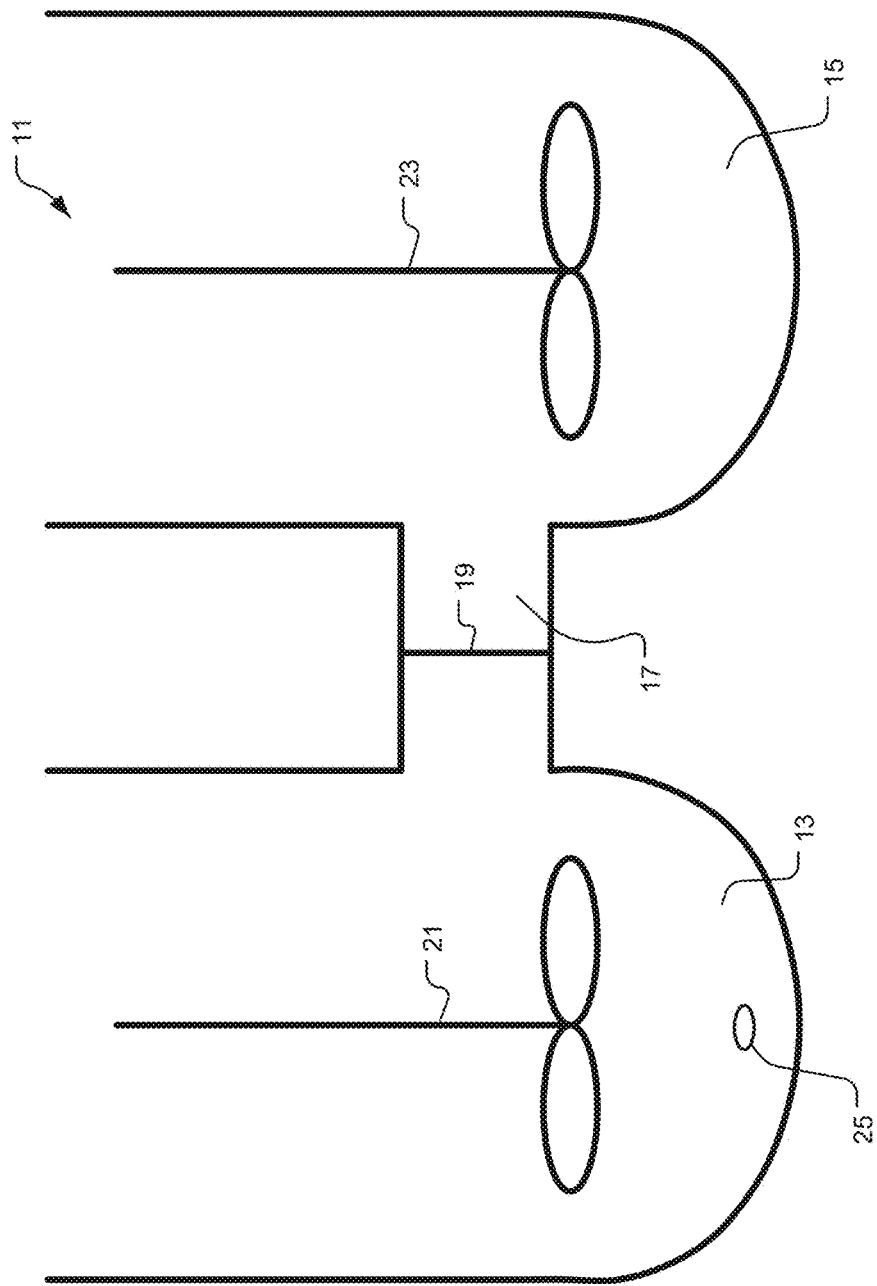
FIG. 1 is a schematic diagram of a side by side arrangement for assessing the dissolution and permeability of a drug product.

Shown in FIG. 1 is conventional arrangement 11, including neighboring chambers, namely donor chamber 13 and acceptor chamber 15. The two chambers are linked by conduit 17 which includes membrane 19. The contents of chambers 13 and 15 are stirred by paddles 21 and 23. During testing, a pharmaceutical compound is supplied to donor chamber 13 in dosage form, for example as tablet 25. Dissolved compound that permeates membrane 19 transfers over to acceptor chamber 15.

Figure 2:
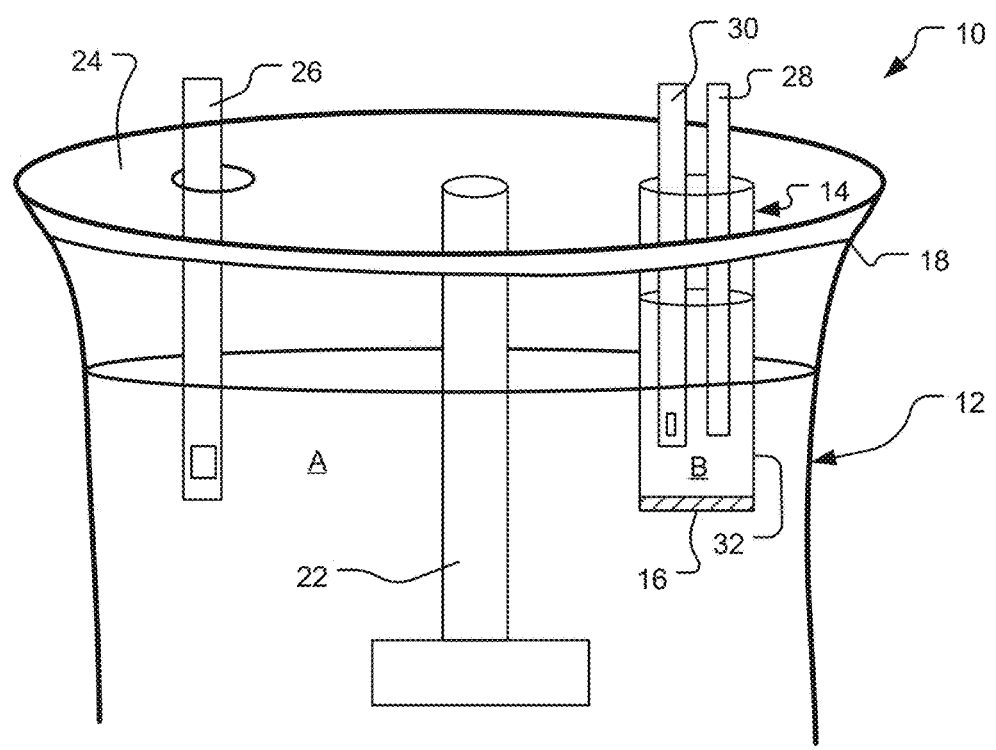
FIG. 2 is a side view of an embodiment of the present apparatus.

Shown in FIG. 2 is apparatus 10, including donor (dissolution) vessel, chamber or compartment 12, receiver (also referred to herein as acceptor or absorption) vessel, chamber or compartment 14 and membrane 16. These components can be thought of as models for in vivo situations. In the case of buccal administration or delivery, for instance, the dissolution vessel represents the oral cavity; the membrane the oral mucosa; and the acceptor vessel the blood circulation.

Donor vessel 12 can have a flared top portion 18 which can be designed to facilitate mounting apparatus 10 into a support such as found, for instance, in a screening or quality control unit or kit. Lip arrangements or other geometries also can be utilized, as can donor vessels having a diameter that varies along the length of the vessel.

As seen in this drawing, at least a portion of the inner vessel (receiver vessel 14) is disposed within (inside) or is "contained" or "immersed" in the outer vessel (donor vessel 12). This type of arrangement is referred to herein as a "nested" arrangement and can include concentric as well as off-center geometries.

The nested arrangement described herein can result in a receiver vessel that is smaller than the donor vessel, facilitating detection of low compound amounts reaching the receiver vessel. Other suitable arrangements include a receiver vessel having a volume that is at least as large as or larger than that of the donor vessel. In one illustration, an immersed cylindrical receiver vessel can have a length (height) sufficiently large to yield a volume equal to or greater than that of the dissolution chamber. Volume ratios between the donor vessel to receiver vessel can be, for instance, 15:1, 10:1, 9:1, 8:1, 7:1, 6:1, 5:1, 4:1, 3:1, 2:1, 1.75:1, 1.5:1 or 1.25:1; 1:1; 1:1.25; 1:1.5; 1:1.75; 1:2; 1:3; 1;4; 1:5; 1:6. 1:7; 1:8; 1:9; 1:10; or 1:15. Other volume ratios can be used. The relative volumes of the two vessels can be optimized considering, for instance, the type of compounds being investigated, detection techniques (smaller volumes of receiver vessel 14 typically increase the concentration of permeated solute and this in turn can facilitate detection), membrane parameters such as membrane type, size, etc., the protocol being followed, kind of support or kit being employed, and so forth. In some implementations, apparatus 10 can be provided with interchangeable receiver vessels 14 that can vary in size, shape, membrane type or size (e.g., if the membrane is provided as an element attached to vessel 14), and/or other parameters.

It is also possible to reverse the function of the two vessels, using the outer vessel as the receiver and the inner vessel as the donor.

The vessels can be constructed from any suitable material that can be individually selected. In many cases, however, both vessels are made from the same material, e.g., plastic, metal, alloys, glass and so forth. In one example, the outer vessel is made of glass while the inner vessel is made of plastic.

Donor vessel 12 and/or receiver vessel 14 can have a curved (e.g., circular, oval, etc.) cross section. Arrangements in which one or both vessels have cross sections that are square, rectangular, diamond-like or have another shape also can be employed. In many instances one or both vessels are cylindrical or substantially cylindrical. One or both vessels can have a bottom that is perpendicular to the length of the vessel, slanted, flat, curved, or having another suitable shape.

In some embodiments, donor vessel 12 is configured to comply with compendial requirements for a dissolution apparatus such as, for example, USP Apparatus I and USP Apparatus II. In other embodiments, donor vessel 12 is configured to fit in a given support such as encountered in screening or quality control equipment. Receiver vessel 14 can have any suitable configuration.

The contents of donor vessel 12 are mixed or agitated using a suitable stirring device 22. This can be a mixing paddle having one or more blades, a magnetic stirrer, a basket housing or encapsulating a compound or product thereof, or another suitable mixer. In specific examples, stirring device 22 is a rotating basket or paddle such as utilized in USP Apparatus I and Apparatus II, respectively. Stirring device 22 can be suspended from lid 24 used to cover donor vessel 12 or can be otherwise supported. It can be connected to a motor or can be driven by a magnetic stirrer plate disposed, for example, at or under the bottom of donor vessel 12.

One or more devices such as probe 26 for measuring conditions or parameters characterizing the contents of the donor vessel can be provided, for example by accessing the interior of donor vessel 12 through an opening in lid 24. If used, probe 26 can be disposed at a suitable position wit13*h* respect to the height of the donor vessel, its diameter, location of the receiver vessel, stirrer location and other parameters. In one implementation, stirring device 22 is a paddle such as utilized in USP dissolution apparatus II and probe 26 is placed about halfway the distance between the top of the paddle and the top of vessel 12.

Receiver vessel 14 is nested in donor vessel 12 in an off center configuration. Off center arrangements include nearly concentric as well as arrangements in which the vertical axis of receiver vessel 14 is far removed from that of donor vessel 12. For instance, receiver vessel 14 can be adjacent to or attached (e.g., via adhesives) to the inner wall surface of the donor vessel. In many embodiments, the two vessels are nested in concentric fashion.

For many applications, receiver vessel 14 is sealed to prevent leakage to and/or from donor vessel 12. If desired, vessel 14 is provided with a stirring device 28 which can be of a type different or the same as stirring device 22 and can be positioned at a suitable location, selected, for instance, in a manner that avoids touching or piercing membrane 16. In some configurations, stirring devices 22 and 28 are mounted on a common shaft or axel. This common shaft or axel can be inserted in the nested vessels through an opening or orifice formed in the permeable membrane. The circumference of the opening can be sealed by O-rings or other suitable means. In concentric designs, the resulting shape of the membrane is that of a donut. In other configurations, stirring device 22 can be a magnetic stirrer while stirring device 28 can be a rotating paddle, blade, or another type of rotor driven system.

Receiver vessel 14 can be provided with one or more devices, such as probe 30, for measuring conditions or parameters characterizing the contents of the receiver vessel. If utilized, probe 30 can be disposed at a suitable location with respect or the height and/or diameter of the receiver vessel, stirrer placement (if a stirrer is utilized), and/or other factors.

Optional probes 26 and/or 30 can be used to identify and/or quantify chemical species, measure temperatures, pH, charged molecules (ions) concentration, conductivity, surface tension and/or other parameters. They can employ fiber optic technology for in situ spectroscopic analysis, ion selective electrode sensors for in situ potentiometric measurements, or other suitable approaches, as known in the art. Alternatively or in addition to, measurements can be performed on aliquots withdrawn from donor vessel 12 and/or receiver vessel 14, in which case the probe is a needle or another suitable device for collecting samples of donor and/or receiving media. Probes utilized for aliquot withdrawal do not need to be a permanent or integral component of the apparatus but can be introduced into and/or removed from one or both vessels as needed, to establish a concentration profile, for example.

In specific embodiments, membrane 16 is positioned at bottom 32 of receiver vessel 14. The placement of bottom 32 and membrane 16 with respect to the height of the dissolution vessel can vary and can be optimized depending on factors such as relative vessel heights, volumes, type of mixing device used, overall hydrodynamics in one or both vessels and/or other considerations. For a paddle type stirrer, for example, membrane 16 at the bottom 32 of receiver vessel 14 is disposed at a height where interference with the paddle is minimized or avoided, e.g., above the paddle provided in the donor vessel, as shown in FIG. 2.

In other arrangements membrane 16 is disposed as a window, at a side wall of vessel 14, or can constitute a portion or an entire wall of the receiver vessel. It may also be possible to fabricate the entire receiver vessel using a suitable membrane. If needed, such a vessel can be held in a perforated support for added rigidity.

Membrane 16 can be any semi-permeable membrane suitable for determining the permeability of a compound in a given system, for instance in a model system for the absorption of an oral dose of a compound. In many cases, the membrane is or mimics an in vivo membrane to be crossed by the compound being evaluated. Artificial as well as natural materials can be utilized, as presently known in the art or as developed by future research. Specific examples include but are not limited to Caco-2 layers, PAMPA membranes, membranes that mimic skin for topical applications, such as, for instance, the membrane used in the Skin PAMPA Explorer™ kit, nasal membranes, and many others. Other suitable types of membranes include size exclusion membranes, such as used in the equilibrium dialysis, for example, lipophobic/lipophilic membranes, mucosal, ocular or corneal membranes, and so forth.

In one implementation, the "membrane" is the interface between immiscible phases. Depending on relative densities, the immiscible phases can form a layered arrangement such as, for example, a bottom layer that is an aqueous solution and a top non-aqueous (e.g., organic) layer. In a specific illustration, the two immiscible phases are water and 1-octanol. Other combinations that can result in immiscible layers producing a membrane interface include but are not limited to water and nonanol, dodecane, hexadecane and so forth.

Membrane 16 can be secured to bottom 22 of receiver vessel 14 using any suitable means. Examples include but are not limited to adhesives, O-ring arrangements, clamps, temperature fusion or other suitable techniques, in particular techniques that prevent leakage between the two vessels. In one example, the membrane is secured in a filter.

The size and/or geometry of the membrane can be optimized taking into consideration factors such as, for example, the size of the apparatus, the volume ratio of the donor and receiver vessel, the permeability of compounds to be tested, detection technique being employed, and so forth.

In some implementations, receiver vessel 14, fitted with membrane 16 and optional components such as probe 30 and/or stirring device 28, can be provided independently. Such a receiver vessel can be configured for being contained or nested, in whole or in part, in an existing donor vessel, e.g., a compendial dissolution vessel, for instance a standard 900 mL container.

Figure 5:
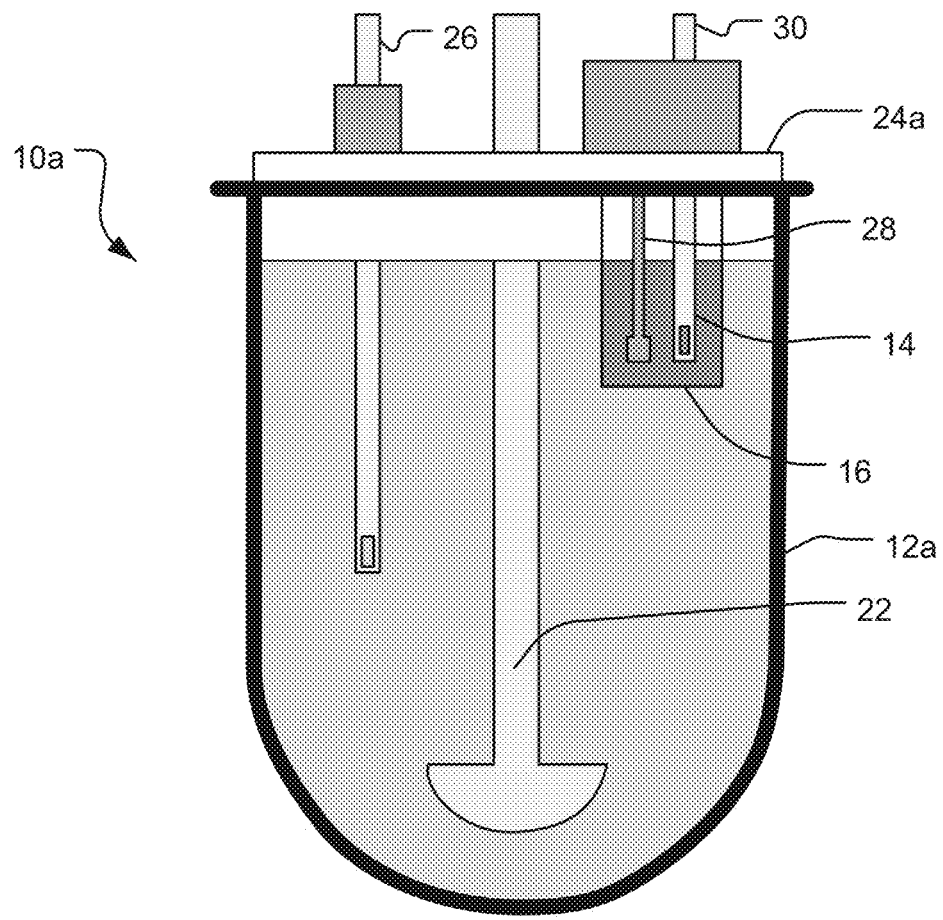
FIG. 5 a vertical cross-section of an apparatus using a compendial donor chamber.

Shown in FIG. 5, for example, is apparatus 10a including compendial USP II donor or dissolution vessel 12a and receiving vessel 14, fitted with membrane 16, e.g., a separating lipophilic membrane. The vessels are covered by lid 24a. Apparatus 10a is provided with stirring devices 22 and 28 and fiber optics probes 26 and 30, essentially as described above. In one implementation, these probes are connected to a Rainbow Dynamic Dissolution Monitor System® (available from Pion Inc., Billerica, Mass., U.S.A.).

During operation, donor vessel 12 and receiver vessel 14 contain, respectively, donor or dissolution medium or solution A (also referred to as "feed" or "dissolution" medium or solution) and receiver medium or solution B (also referred to as "permeate", "receiver" or "acceptor" medium or solution). In many cases, the volume occupied by medium B is smaller than that occupied by medium A. Ratios can be similar to those described above with respect to the relative volumes of vessels 12 and 14, for example, 15:1, 10:1, 9:1, 8:1, 7:1, 6:1, 5:1, 4:1, 3:1, 2:1, 1.75:1, 1.5:1 or 1.25:1. The volume occupied by medium B also can be the same or larger than that occupied by medium A, with illustrative ratios of the volume of A to B of: 1:1; 1:1.25; 1:1.5; 1:1.75; 1:2; 1:3; 1;4; 1:5; 1:6. 1:7; 1:8; 1;9; 1:10; or 1:15, for example.

The two media can be selected to mimic in vivo conditions found on the opposite sides of a membrane of interest.

In some cases, one or both solutions are water-based or aqueous solutions. Medium A and/or B also can be organic solutions. One or both media can contain additives and can be controlled for pH, temperature, viscosity, osmolality, and/or other parameters.

In an illustrative example, solution A is an in vitro model for the contents of the human gastrointestinal tract; solution B is an in vitro model of the human bloodstream; and membrane 16 is an artificial membrane mimicking properties of gastro-intestinal epithelial barrier, e.g., one is used in Double-Sink™ PAMPA from Pion, Inc., Billerica, Mass., U.S.A. In vitro models for various in vivo systems are known in the art or can be developed or adapted to specific circumstances. In another illustrative example, the membrane and techniques utilized are those described in U.S. Pat. No. 7,022,528 issued to Avdeef, et al. on Apr. 4, 2006, the contents of which are incorporated herein by reference in their entirety.

A compound to be evaluated is introduced into dissolution medium A, in donor vessel 12; at the onset of the experiment, acceptor medium B, in receiver vessel 14, is free of the compound. The compound can be in neat (pure) form or can be a component in a compound product, typically a formulation or mixture containing not only the compound under study but also excipients and/or other active and/or non-active ingredients. In one example, the compound product is a dosage form of a pharmaceutical ingredient, for example a tablet, caplet, capsule or another type of compacted solid. Viscous materials such as found in gel caplets also can be investigated, as can loose powders, liquids, patch formulations, sublingual strip formulations or other forms of a compound.

The compound (neat or as part of a compound product) can be poured, released or dropped (e.g., as a tablet) into medium A. In other approaches, the compound is provided in a suitable holder, for instance, a basket, such as found, for instance, in the USP I Apparatus, or another suitable support or housing designed to allow direct contact between the compound and medium A.

For a soluble or partly soluble compound, as dissolution occurs and depending on the permeability of dissolved compound through membrane 16, part of the solute transfers from the medium A, in donor vessel 12, to medium B, in receiver vessel 14. Over time, this transfer can be reflected in a decrease of solute amounts in the donor vessel and an increase in solute amounts in the receiver vessel. Amounts of dissolved compound (also referred to herein as solute) in vessels 12 and 14 can be measured using various techniques, such as, for example, high performance (pressure) liquid chromatography (HPLC), potentiometric techniques, ultraviolet, emission (e.g., fluorescence), infrared (IR), near-IR spectroscopy, polarography, electron paramagnetic resonance (EPR) or electron spin resonance (ESR) spectroscopy, mass spectroscopy (MS), nuclear magnetic resonance (NMR) and others.

In specific embodiments, solute concentrations are measured in situ (using, for example, probes 26 and/or 30), on a continuous basis. Approaches that can be utilized are described, for example, in U.S. Pat. Nos. 6,174,497 and 6,558,957 and issued to Roinestad, et al. on Jan. 16, 2001 and May 6, 2003, respectively, the contents of which are incorporated herein by reference in their entirety. Series of distinct in situ measurements also can be obtained, e.g., at desired time intervals. In other approaches, measurements are conducted by withdrawing aliquots from vessel 12 and/or 14. Other procedures can be employed.

Similar approaches can be utilized to determine a concentration profile (i.e., the amount of compound or compound product present as a function of time) when the material of interest is in liquid or viscous form, such as, for instance, in the case of a liquid compound that is completely miscible with the donor medium. Concentration profiling also can be conducted for liquid compounds or compound products that are only partly miscible or immiscible with the donor medium.

Amounts (if any) trapped in the membrane can be determined by mass balance calculations or other suitable techniques.

Probes and measurement techniques described herein can be extended to monitoring not only the compound but one or more other (additional) ingredients (active or inactive) present in a compound product or separately introduced in the donor vessel 12.

Data can be collected and handled by an operator, by using computerized methods or through a combination of the two. In many cases, the information obtained is compared with calibration plots establishing a relationship between measured signal and compound concentrations. In some embodiments, calibration curves are determined in the same apparatus (to account, for example, for the nested arrangement or other parameters or artifacts specific to the set-up). Calibration curves for dissolution rates in an apparatus such as apparatus 10 can be obtained, for instance, by blocking membrane 16 or by other approaches. In some cases, an existing calibration curve is modified by taking into account previously established apparatus-specific parameters. Other protocols can be employed.

In an illustrative example, one or more standard compounds known to display or share a given behavior (e.g., high solubility-low absorption, low solubility-high absorption, etc.) are tested to obtain concentration measurements as a function of time in the two vessels. The plots obtained can then be used as reference plots for comparing and classifying (e.g., according to the BCS system) the substance being evaluated.

Typically, limiting factors for (in vivo) bioavailability are solubility, dissolution rate and permeability. A compound that is highly water-soluble, for example, can easily dissolve in the aqueous environment of the gut. However, this high solubility in aqueous solutions may hinder passage across lipophilic membranes like the gastrointestinal lining. In contrast, low water-solubility hinders dissolution, but allows compounds to pass more freely across the membrane. Thus dissolution and/or permeability rates obtained as described above can be helpful in predicting in vivo behavior. In some embodiments, in vivo behavior is predicted using established or newly developed correlation techniques or models such as, for instance, models implemented in commercially available software packages such as GastroPlus™ from Simulation Plus, Inc. (a simulation tool that predicts the absorption, pharmacokinetics, pharmacodynamics, or other properties for drugs administered through intravenous, oral, ocular, or pulmonary routes), PK-Sim® from Bayer or others. It is also possible to further refine or adapt existing models to more accurately predict in vivo behavior using the apparatus and method described herein. In one implementation, the techniques used are described in U.S. Pat. No. 8,175,815, issued to Avdeef, et al. on May 8, 2012, the contents of which are incorporated herein by reference in their entirety.

Approaches described herein can yield information on the absorption potential of the compound (or compound product) being investigated. For instance, approaches and equipment described herein can be used to characterize and/or predict in vivo absorption potential of a compound, often an active pharmaceutical ingredient or API, or a product containing the compound, e.g., the API. Embodiments disclosed herein relate to measuring an in vitro absorption potential, a parameter that could be expressed, for example, in the form of flux through the permeation membrane (i.e. amount of API penetrating through the membrane per unit area per unit time, e.g., in $mg*min^{-1}*cm^{-2}$ units); total amount of material permeated to the receiver compartment during a particular time period (e.g., in mg units); relative amount of drug permeated to the receiver compartment (e.g., in %); or another parameter that would directly or indirectly include in itself dependence on solubility of API, dissolution or precipitation rate of API and permeability of API. Differences between compounds or compound formulations that could be relevant to in vivo absorption can be evaluated by comparing the absorption potential parameters characterizing a first and second compounds or compound products. For instance, the first compound or compound product could be the API under investigation, while the second compound or compound product could be a material with a known absorption potential parameter, e.g., a reference or standard material. In other situations, the absorption potential of a compound (API) in neat form (or in a product or formulation) is compared to the absorption potential of the compound in one or more different formulations.

In specific implementations, effect of permeation on dissolution rate is assessed by measuring changes in the concentration versus time behavior in both donor and receiver compartments. In the absence of permeation to receiver vessel 14, the concentration in the donor chamber typically increases, eventually reaching a maximum value (depending, for example, on the solubility of the compound or compound product in medium A). The rate of permeation of the compound (or compound product) to vessel 16, however, can affect the dissolution behavior observed in donor vessel 12. For example, the concentration observed in donor vessel 12 as a function of time can exhibit different rates of increase, can decline and/or reach a maximum at a different point in time relative to plots observed in the absence of permeation. Turning to receiver vessel 14, solute concentration typically increases with time. The slope of this curve is proportional to the flux, i.e., the rate of diffusion or transport of the compound across permeable membrane 16. The difference in the dissolution behavior in the presence of absorption chamber can be used to determine what parameter, namely, dissolution rate, solubility or permeability is a limiting factor for absorption of the studied drug.

This technique is not restricted to a particular configuration of the donor-receiver vessels (compartments) and can be utilized, for example, in nested arrangements such as, for instance, those described above, in side by side (e.g., adjacent or in close proximity) donor-receiver systems, and so forth. In many embodiments, the technique described herein is conducted in an apparatus in which the receiving vessel is immersed (partially or completely) in the dissolution medium.

Figure 8:
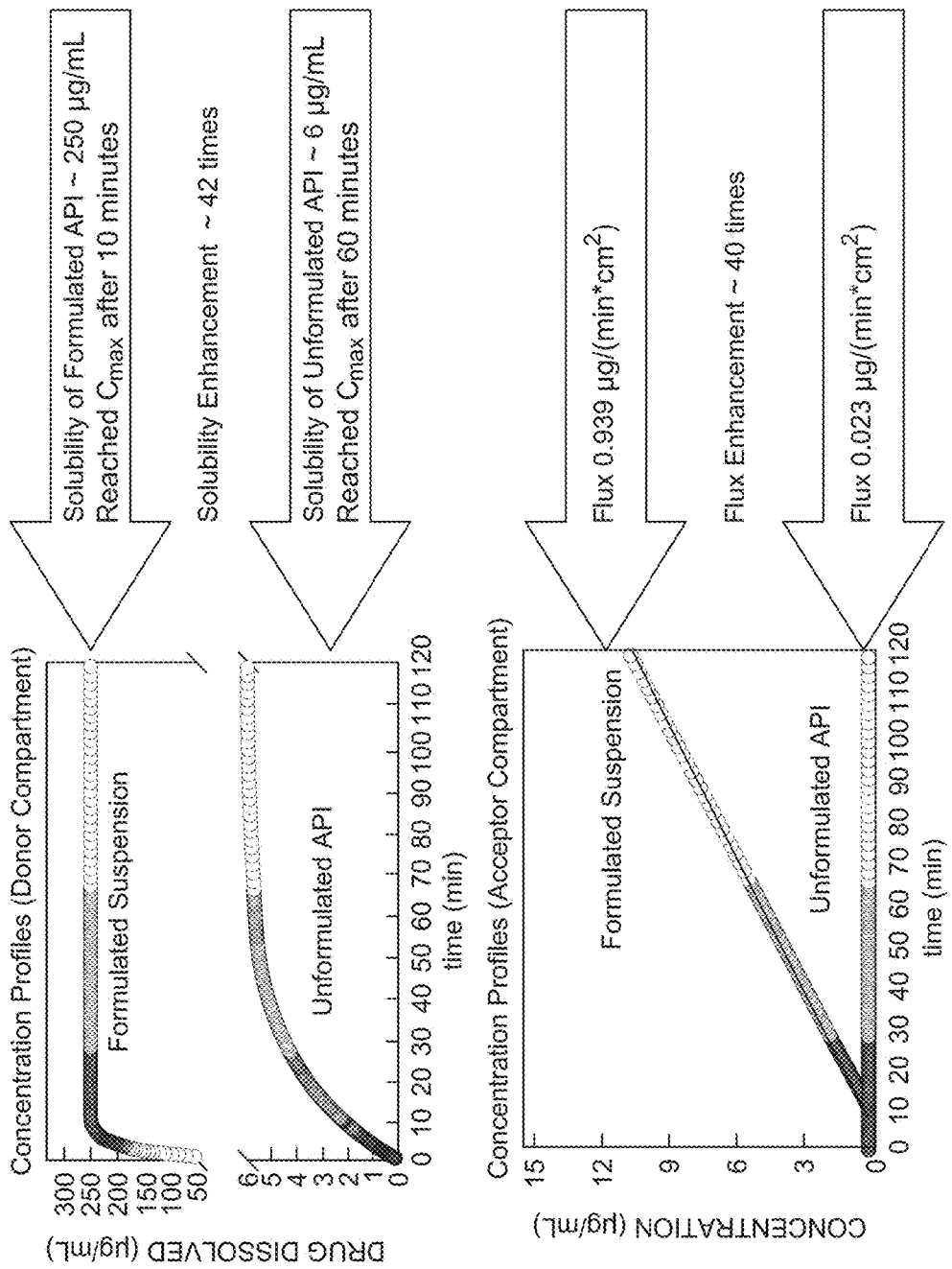
FIG. 8 is an illustration of a case in which increasing the concentration of the compound in the donor medium causes an adequate increase in absorption potential measured through flux.
Figure 9:
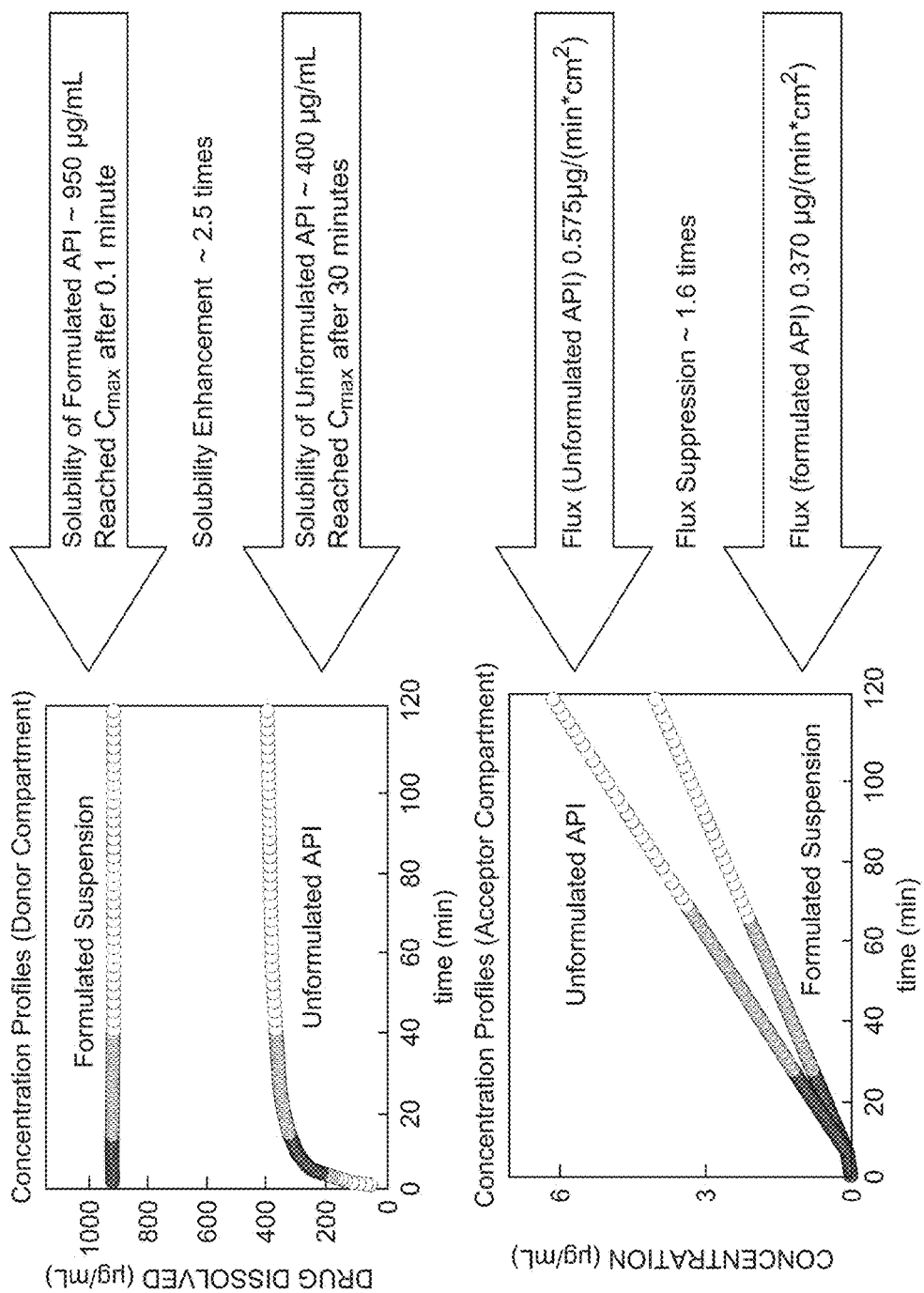
FIG. 9 is an illustration of a situation in which increasing the concentration in the donor medium through drug formulations can lead to decreasing the absorption potential measured through the flux.

Illustrative applications of the techniques are described with reference to FIGS. 8, 9, 10 and 11. In the specific situations depicted in FIGS. 8 and 9, for example, in vivo relevant changes in the dissolution rate and maximum reached concentration (that could or could not be limited by the solubility of the compound) are assessed by the effect of such changes on the absorption potential expressed by flux. As shown in FIG. 8, the increase of maximum concentration causes the quantitatively similar increase in the flux of the studied compound through the membrane. In contrast, the example shown in FIG. 9 demonstrates that despite the increase in the dissolution rate and maximum reached concentration for the formulated API, the flux of this compound through the membrane decreased compared to the unformulated API. In the drug development process, formulations depicted on FIGS. 8 and 9 would be considered, respectively, as favorable and unfavorable based on the absorption potential change they caused.

Figure 10:
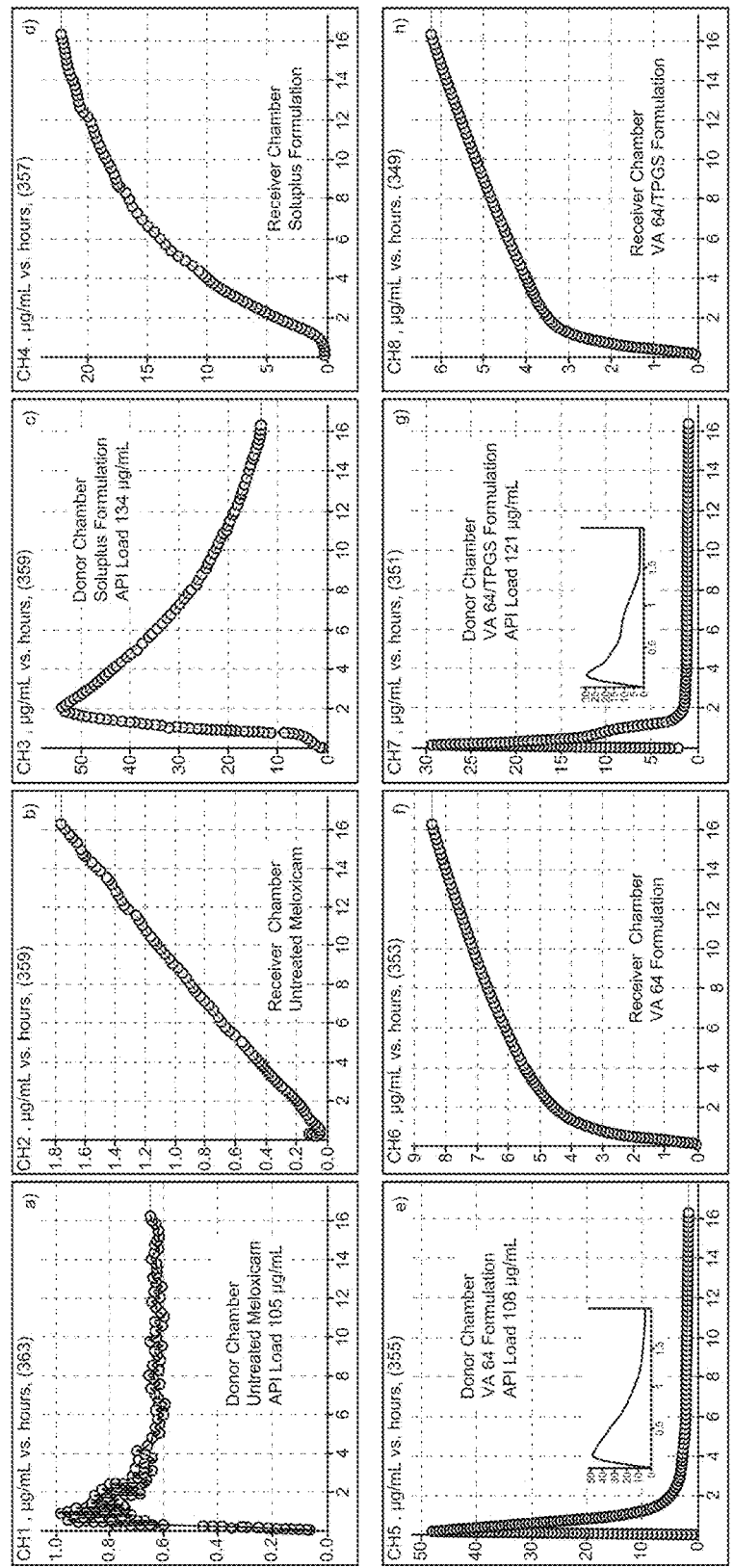
FIG. 10 is a series of concentration-time profiles of meloxicam (μg/mL vs. hr) in donor compartments or vessels a), c), e), g) and receiver chambers or vessels b), d), f), h) in the combined dissolution-permeation assay. Inserts in e) and g) zoom in into first 2 hours of the assay to highlight peculiarities of supersaturation phase for corresponding formulations.
Figure 11:
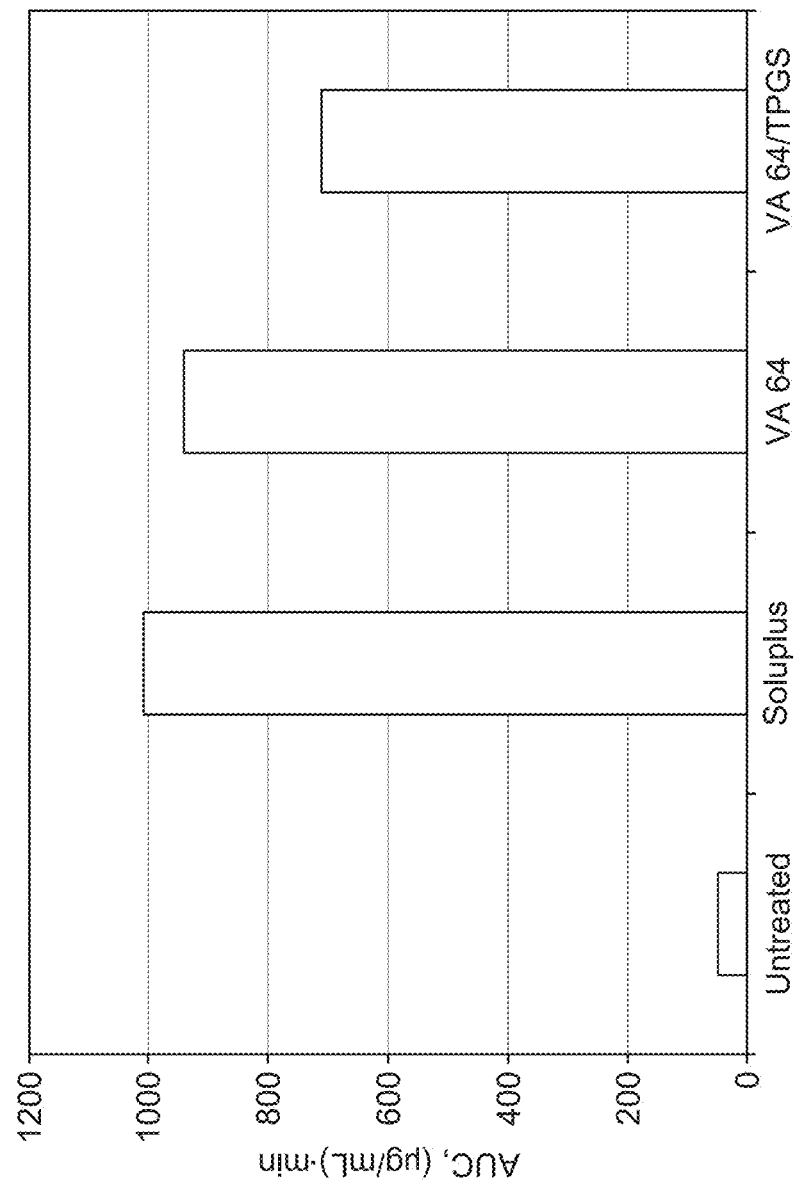
FIG. 11 is an illustration pertaining to complex effects of formulations, effects that could be assessed by comparing the absorption potential of the formulations expressed as area under concentration versus time profile in the receiving compartment or vessel. The values correspond to the meloxicam formulations shown on FIG. 9.

In another specific illustrative example, depicted in FIG. 10, a low soluble compound, meloxicam (API) is formulated as amorphous solid dispersions (ASD formulations) with different polymers to improve kinetic solubility and subsequent dissolution rate of API. While ASD formulations can form so-called "supersaturated" solution where the API concentration exceeds its equilibrium solubility of crystalline form, such solutions are thermodynamically unstable and API eventually precipitates as crystalline material. The in vivo relevance of these kinetic transformations is difficult to assess by monitoring concentration in the dissolution vessel alone. However, they can be studied through a comparative analysis of absorption potential change that such formulations cause. For instance, total cumulative amount of API in the receiving medium at a certain time point or area under the concentration-time profile in the receiving medium, as shown in FIG. 11, can be used as the absorption potential.

The apparatus described herein can be incorporated in a kit (or unit) for assessing dissolution or both dissolution and permeability. Such kits can be configured for compatibility with existing units or can have a different design. The operation of the kit can be manual or automated and data collection and/or handling can be computerized using existing or newly developed techniques.

In addition or alternatively, existing procedures for using a pH gradient such as relied upon in the Double-Sink™ method, available from Pion, Inc., Billerica, Mass., U.S.A. in its PAMPA Explorer™ kits, can be adapted to the method, apparatus or kit described herein.

In some of its specific aspects, apparatus 10, optionally integrated in a kit, is configured and operated to meet existing or future standards for determining and/or reporting properties of pharmaceutical and related compounds. The U.S. Pharmacopoeia, for example, provides various designs and protocols for studying drug dissolution properties. In some implementations, the present apparatus and method are configured or adapted for integration with or replacement of USP I and II dissolution vessels (basket and rotating paddle, respectively). In other implementations the apparatus and method described herein comply with requirements specified in the Japanese, European Union or other national or regional Pharmacopoeias. In further implementations, the present apparatus and method are configured and operated to meet standardized protocols such as those encountered during long term stability studies (LTSS) in the context of New Drug Applications (NDA) before the Federal Drug Administration (FDA) or other situations.

Other designs in which one vessel is contained in the other can be used to combine the assessment of dissolution and permeability. Shown in FIG. 3, for example, is apparatus 51, including donor vessel 53, receiving vessel 55 and membrane 61. Optionally, vessel 53 has lip 59 designed, for example, to fit in a support, e.g., a kit rack. Receiving vessel 55 is configured as a pocket contained in donor vessel 53.

The wall separating the two vessels, wall 57, can be made out of a suitable material that is the same or different from that utilized to fabricate donor vessel 53. In one example, both wall 57 and donor vessel 53 are made from the same plastic material, e.g., by molding.

Membrane 61, essentially as described above, is provided in an opening in wall 57. In other implementations, wall 57 is fabricated in whole or in part of a membrane material. Stirrers 63 and/or 65, as well as probes 67 and/or 69, essentially as described above, can be optionally included. Apparatus 51 can be integrated in a kit and can be operated as discussed with reference to FIG. 2.

The present apparatus and method are further described in the following non-limiting examples.

Example 1

Figure 3:
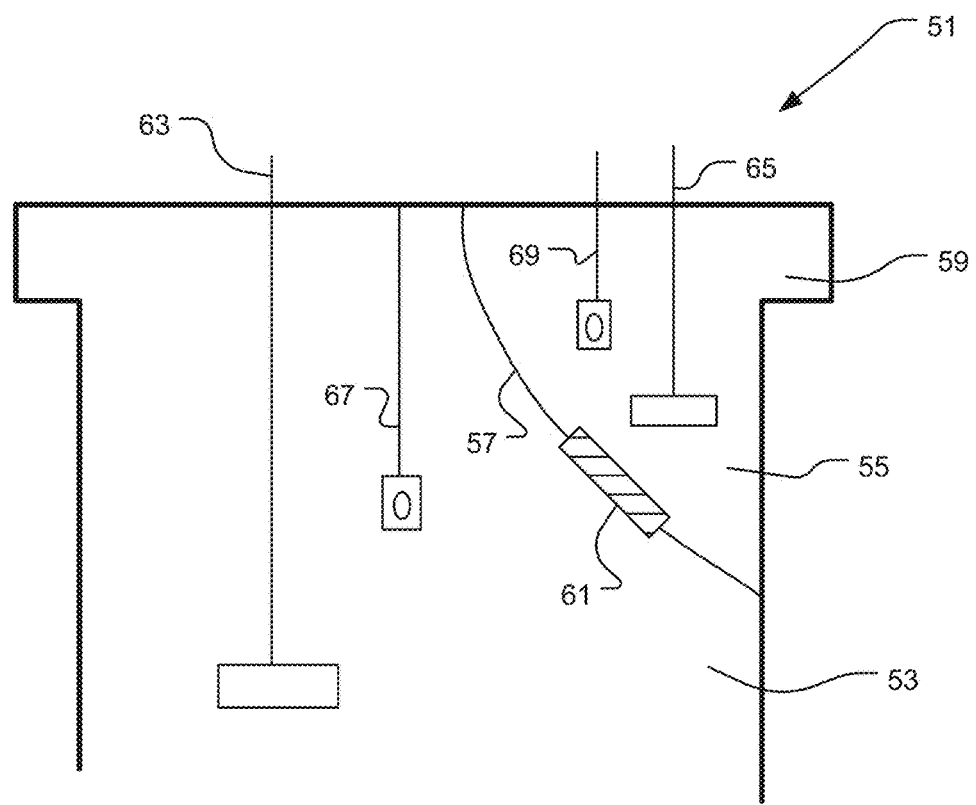
FIG. 3 is a vertical cross-section of an apparatus having an inner pocket receiver.

This study was undertaken to explore and compare the hydrodynamics in an apparatus in which the receiver vessel is a tube immersed in the donor vessel; an apparatus in which the receiver vessel is a cylinder nested in the donor vessel in a concentric arrangement; an apparatus having a side pocket configuration as in FIG. 3; and a USP apparatus 2, which served as a control. In addition, three other arrangements also were included: a traditional dissolution vessel using a partial blade; a dissolution vessel using a double blade; and a dissolution vessel connected to an outer receiver vessel, the latter vessel having the shape of an outer tube protruding or extending from the donor vessel, as described with reference to FIG. 4.

Figure 4:
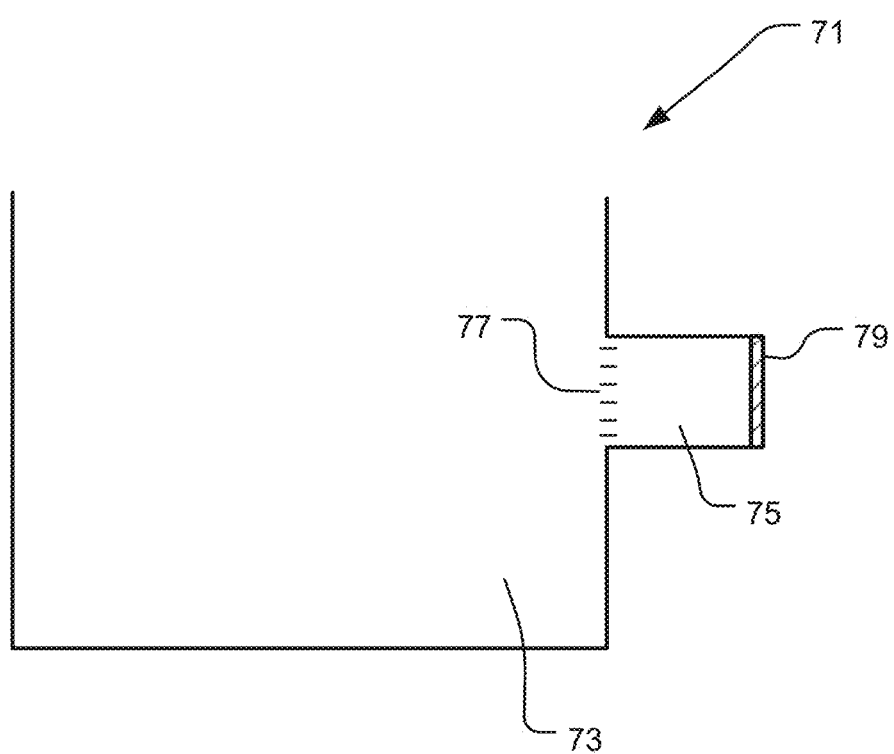
FIG. 4 is a vertical cross section of an apparatus including an outer side tube.

Shown in FIG. 4 is apparatus 71 including donor vessel 73 and receiver vessel 75, protruding outwardly, separated by membrane 77. Donor vessel 71 can be provided with probes and a mixing device, essentially as described above and can be configured as already discussed, e.g., for integration into a support or kit. Receiver vessel 75 is in the shape of a tube or can have another suitable protruding geometry. Its outer opening is closed, for example by cap 79. If desired, receiver vessel 75 can be smaller than the donor vessel, this feature helping to increase detection of low levels of permeated solute. In contrast to the embodiments of FIGS. 2 and 3, the protruding geometry may complicate the mixing process in the receiver vessel.

The compound used was a non-commercial form of metformin HCl tablet (dose of 125 mg) in a water dissolution medium held at 37° C. Mixing was by a paddle type stirrer rotated at 50 rpm for 1 to 10 minutes, then at 100 rpm. The experiment was performed in the USP Apparatus 2.

Figure 6:
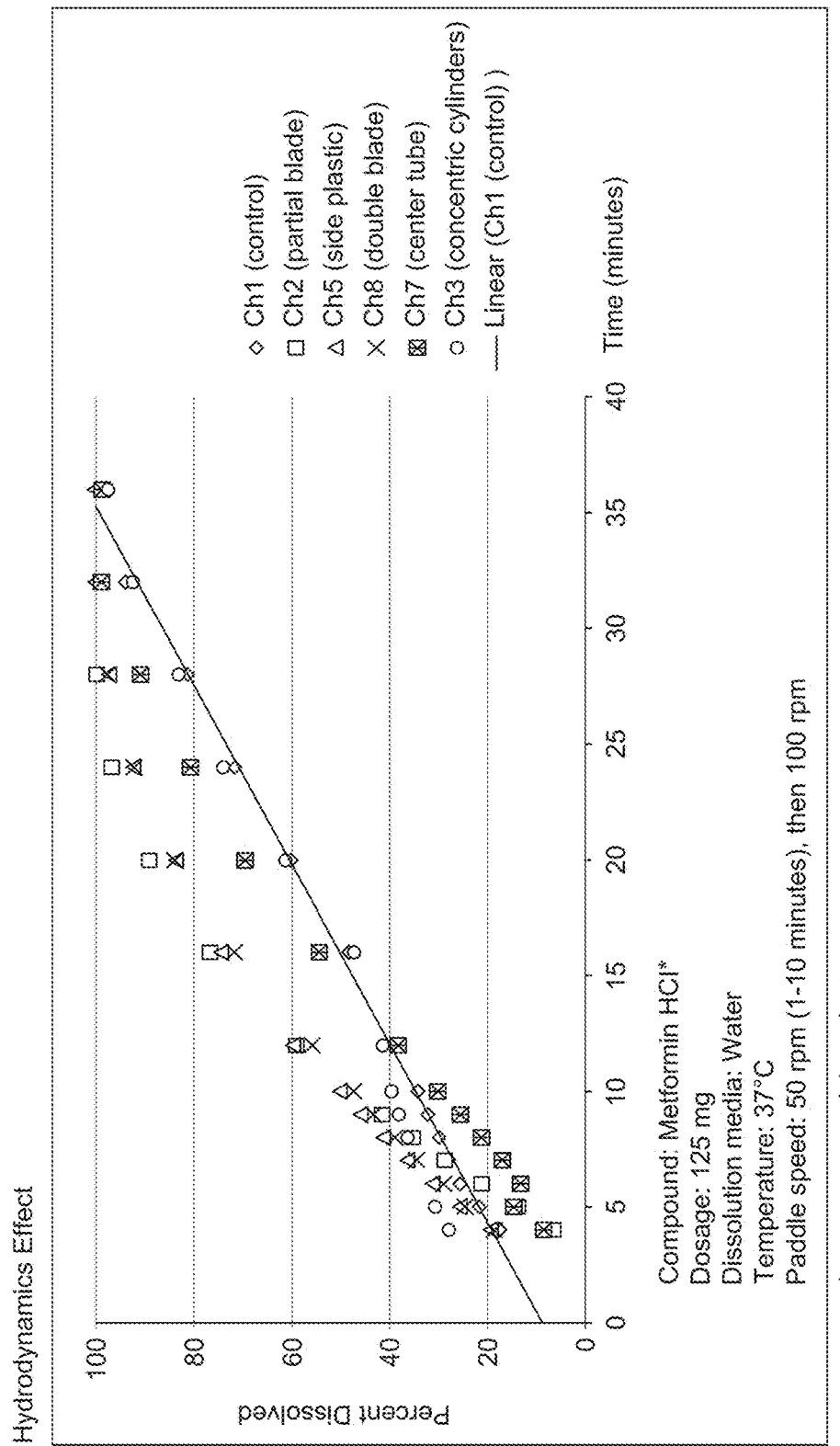
FIG. 6 is a series of plots indicating hydrodynamics for several apparatus configurations.

The data are presented in FIG. 6 and indicated that several configurations displayed good hydrodynamics, with best results being provided by the immersed center tube and concentric cylinders arrangements.

Example 2

A concentric nested arrangement was used to study permeability of several compounds. The membrane was a PAMPA membrane and experiments were performed with and without Acceptor Sink Buffer™ on the acceptor sink side. Concentrations measurements were taken using in situ UV fiber optic system Pion Spectra™.

The compounds tested and some of their properties (including the values for the octanol-water pH-independent partition coefficient (as log P)), and the dosages employed are shown in Table 1.

TABLE 1

| Compound | Molecular Weight (g/mol) | Log P | Dosage (mg) |
| --- | --- | --- | --- |
| Metformin HCl | 165 | 0.05 | 850 |
| Aspirin | 180 | 1.19 | 100 |
| Caffeine | 194 | −0.07 | 100 |

Effective permeability coefficients ($P_{eff}$) are shown in Table 2.

TABLE 2

| Compound | $P_{eff}$ (cm/second) |
| --- | --- |
| Metformin HCl | 3.6025E−05 |
| Aspirin | 3.31E−04 |
| Caffeine | 2.57E−04 |

The results indicated that in this type of apparatus, model compounds permeated as expected:

Aspirin=caffeine>metformin

Example 3

Experiments were conducted to investigate whether an arrangement such as that of apparatus L (nested concentric donor and receiver vessels) can distinguish between slow and fast release behaviors. The samples used and their properties are shown in Table 3 below.

TABLE 3

| Drug | Rate of QC Release | Appearance Rate (µg/mL/min) |
| --- | --- | --- |
| Caffeine | Fast | 0.0014 |
| Caffeine | Slow | 0.0007 |

Figure 7:
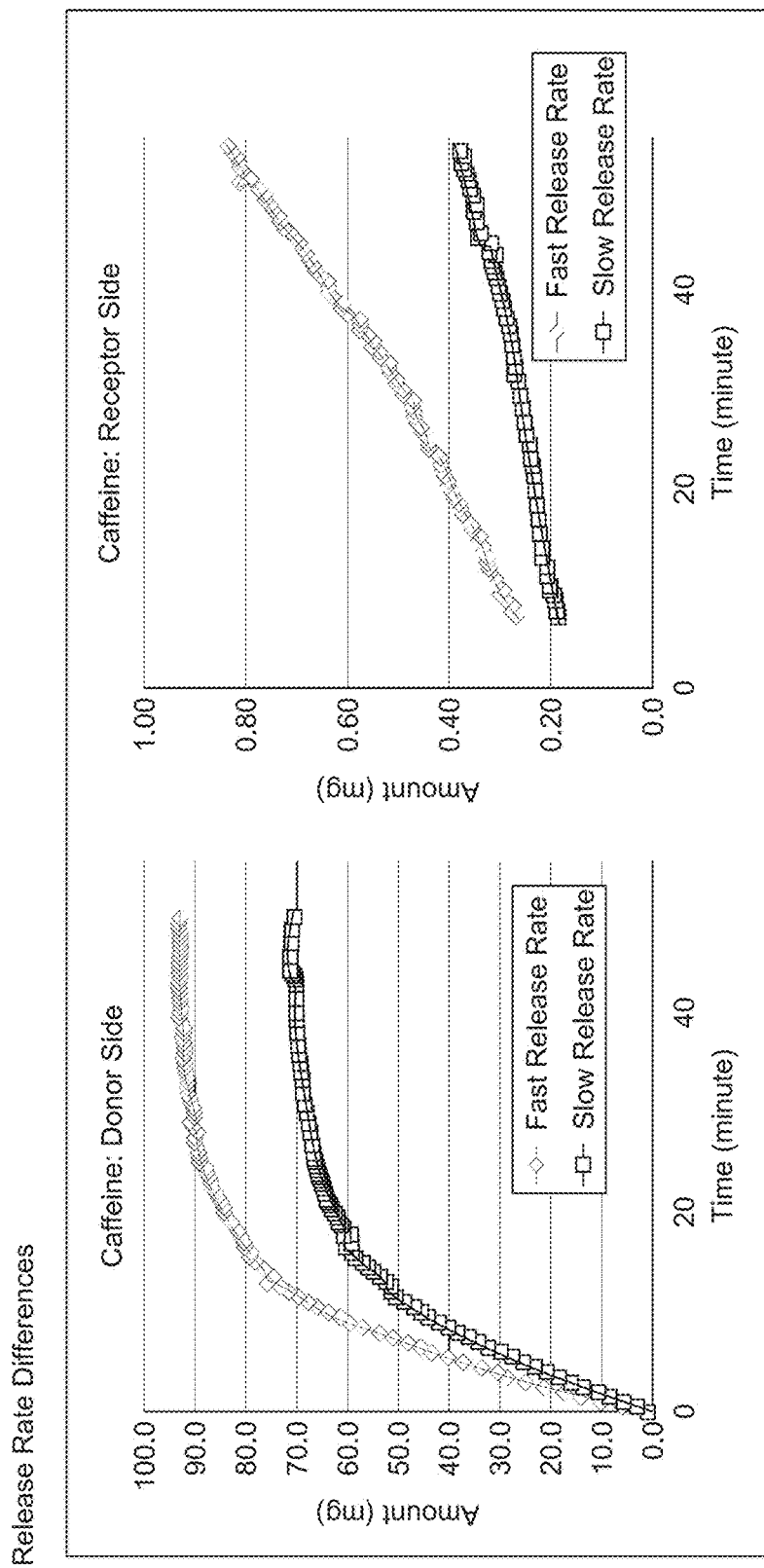
FIG. 7 is a series of plots showing drug amounts (mg) as a function of time (minutes) of fast release and slow release caffeine formulations in the donor and receiver vessel of an apparatus such as that shown in FIG. 2.

Observed concentrations (sampled as described in Example 2) of the fast and slow formulations in the two vessels are plotted in FIG. 7. The data showed that a configuration such as that of apparatus L can be used to discriminate between fast and slow release behaviors in both donor and receiver vessels.

Example 4

The following experiments were conducted in side-by-side apparatus similar to one shown on FIG. 1 or FIG. 12 (further described below) but with smaller volume to investigate how different formulations of low soluble compound meloxicam can be compared based on their absorption potential. The following API and amorphous solid dispersions (ASD) formulations were studied:

Untreated crystalline Meloxicam
15% Meloxicam/85% Soluplus ASD
15% Meloxicam/85% Kollidon VA64 ASD
15% Meloxicam/72.5% Kollidon VA64/12.5% Kolliphor TPGS ASD Results for untreated Meloxicam in the donor and receiver vessels are shown, respectively, in FIGS. 10 *a*) and 10 *b*). It can be seen from FIGS. 10 *c*), 10 *e*) and 10 *g*) that the concentration of API in all donor vessels (chambers or compartments), where ASD formulations were introduced, exceeded the concentration of crystalline API (FIG. 10 *a*)) in the initial phase. However, API started precipitating with different rates in those donor vessels. This caused a dynamic change in flux as indicated by the changing slopes in the concentration versus time profiles in the receiving chambers (FIG. 10 d), f) and h)). It is thought that in such complex situations the formulations can be compared by either the area under the concentration-time profile in the receiving vessel, as shown on FIG. 11, or even more simply, by comparing the cumulative amount of API in the receiving vessels after a certain period of time.

Example 5

Since among the newly discovered active pharmaceutical ingredients the number of poorly water soluble candidates is continually increasing, dissolution enhancement of poorly water soluble drugs has become one of the central challenges of pharmaceutical studies. So far the preclinical studies have been mainly focused on formulation methods to enhance the dissolution of active compounds, in many cases disregarding the fact that the formulation matrix not only affects dissolution but also has an effect on the transport through biological membranes, changing permeation of the drug molecules. The aim of this study was to test an electrospun cyclodextrin-based formulation of aripiprazole, having the molecular structure shown below, using a techniques that monitors permeation together with dissolution, thus achieving a better understanding of the in vitro-in vivo correlation.

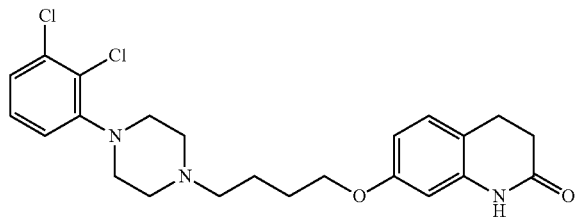 [SMILES: O=C1CCc2ccc(OCCCCN3CCN(c4cccc(Cl)c4Cl)CC3)cc2N1]

Preparation of the cyclodextrin-based electrospun formulation of aripiprazole and other experimental details are described by E. Borbas et al. in *In Vitro Dissolution-Permeation Evaluation of an Electrospun Cyclodextrin-Based Formulation of Aripiprazole Using µFLUX™*, International Journal of Pharmaceutics, vol. 491, pp. 180-189 (2015), the contents of which are incorporated herein by reference in their entirety.

The µFLUX™ apparatus utilized is available commercially from Pion Inc., Billerica, Mass., U.S.A. As shown in FIG. 12, the apparatus included, respectively, donor and an acceptor chambers 81 and 83 (20 mL volumes) separated by artificial membrane 85 (PVDF, polyvinylidenefluoride, 0.45 mm, 8.55 $cm^2$). In the case of buccal drug delivery, the donor chamber represented the oral cavity, the artificial membrane the oral mucosa, while the acceptor chamber represented the blood circulation. At first 75 mL of n-dodecane was dribbled on the membrane surface, then 20 mL of pH 6.8 phosphate buffer was added into the donor chamber, and 20 mL of sink buffer was added into the acceptor chamber. The solubility of ARP is 30 mg/L in the acceptor buffer, which meets the requirement for sink condition, i.e. the volume of medium in the acceptor chamber is at least three times greater than required to form a saturated solution of the drug substance (FIP Guidelines, 1981, USP 23, 1995). Samples equivalent to 20 mg of ARP were placed in the donor chamber. Both chambers were stirred at 200 rpm at room temperature, using stirring devices 87 and 89. The temperature was controlled via elements 91. In both chambers the API concentration was followed by UV-spectrophotometry at 252 nm. Suitable probes for the spectroscopic measurements (not shown in FIG. 12) were introduced through openings 93 and 95.

The flux across the membrane was calculated using the following equation:

$$J(t) = \frac{\Delta n}{A * \Delta t}$$

where the flux (J) of a drug through the membrane is defined as the amount (n) of drug crossing a unit area (A) perpendicular to its flow per unit time (t).

Figure 13A:
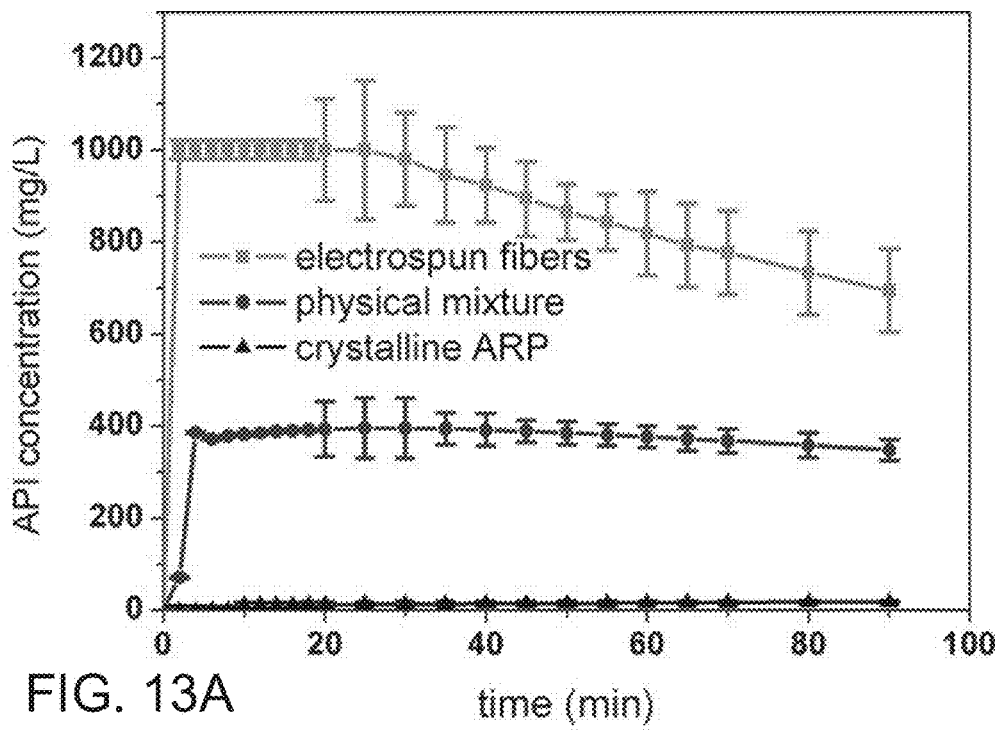
FIGS. 13A and 13B show, respectively, API concentrations of different forms of aripiprazole in the donor compartment and the acceptor compartment of an apparatus such as that in FIG. 12.

It was found that a cyclodextrin-based electrospun formulation of aripiprazole had the potential to ensure fast drug delivery through the oral mucosa owing to the ultrafast dissolution of the drug from the formulation and the enhanced flux across membranes as shown by the result of the in vitro dissolution and permeation test. The API concentration profiles in the donor and acceptor vessels (1000 mg/L max concentration, 0.025 mol/$dm^3$ $KH_2PO_4$ buffer in the donor compartment, n-dodecane membrane, sink buffer as acceptor, 150 rpm, 25° C.) are presented, respectively, in FIGS. 13A and 13B.

The results of in vitro dissolution-permeability measurement on the µFLUX™ platform showed that the complete dissolution of the API from the sulfobuthylether-b-cyclodextrin-based (SBEbCD-based) formulation was reached within only 2 min (FIG. 13A), meaning an ultrafast dissolution, much faster than that observed with the pure API. In fact, the dissolution rates of the pure API and the electrospun fibers API formulation differed by two orders of magnitude. During the biorelevant time (30-60 min in the case of buccal or sublingual formulations) from the crystalline form, only 1.5% of the API was able to dissolve, while from the electrospun formulation the dissolution was 100%. In comparison with the dissolution tests, where precipitation of the drug molecules was perceptible after 20-30 min, precipitation, which started here at a similar time point, was much slower and less dramatic. After 60 min about 80% of the drug molecules were in solution, meaning that less than one fifth of the ARP molecules precipitated from the supersaturated system, while in the case of the dissolution tests only one fifth stayed in solution during that time. This improvement could be caused by the presence of the artificial membrane. Namely, both the transport through the membrane and the precipitation of the drug could lower the concentration of ARP in the supersaturated system. Therefore, the transport and the precipitation became competitive processes, such as ionization and complexation of ARP molecules. As a result the ratio of precipitated molecules is lower when the artificial membrane is present.

Figure 13B:
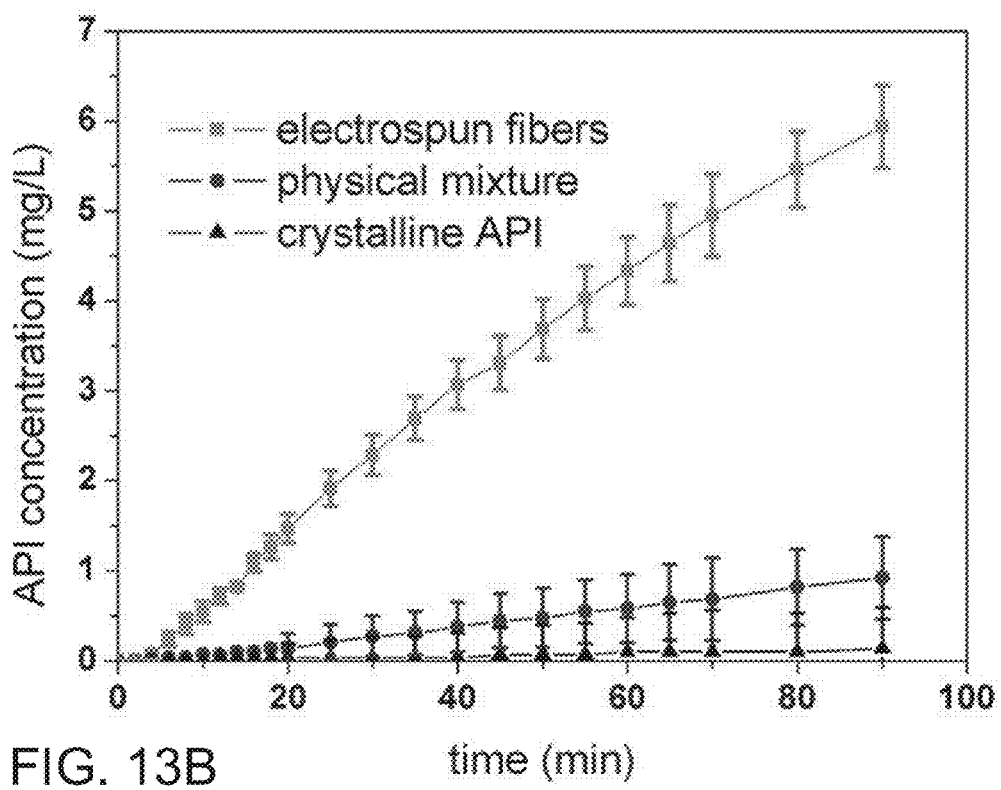

On the acceptor side of the artificial membrane the API concentration was significantly higher in case of electrospun fibers than the physical mixture or the crystalline ARP (FIG. 13B). This difference between the formulated and non-formulated form also could be noticed from their flux. The flux during the first 25 min was found to be 767 µg/h×$cm^2$ in the case of the electrospun sample, in contrast to 82 µg/h×$cm^2$ for the physical mixture and 16 µg/h×$cm^2$ for the crystalline form. This means that approx. 50 times more molecules went through the membrane from the electrospun formulation matrix than from the crystalline form. Although there were many factors influencing the solubility-permeability interplay (such as the use of excipients like cyclodextrins and polymers, the fair amount of the ionized form present in the donor compartment, which actually necessitated the dissolution-permeation tests) this type of formulation not only improved the dissolution, but also significantly increased the amount of permeated drug molecules, as shown by the above results. The enhancement of the dissolution rate of the formulation compared to the pure API and the enhancement of the concentration in the acceptor compartment differ appreciably owing to the influencing factors mentioned earlier. These results point out how important it is to study both dissolution and permeation properties of formulations together, e.g., simultaneously and taking into consideration the solubility-permeability interplay, especially when formulating poorly water soluble APIs.

Example 6

The aim of this study was to investigate the impact of formulation excipients and solubilizing additives on dissolution, supersaturation and membrane transport of active pharmaceutical ingredients (API). When a poorly water-soluble API is formulated to enhance its dissolution, additives, such as surfactants, polymers and cyclodextrins have an effect not only on dissolution profile, but also on flux through relevant membranes. In order to fully understand these effects on flux, the driving force of membrane transport cannot be simplified to the total concentration gradient, but has to be considered as thermodynamic activity of the drug.

Meloxicam (abbreviated herein as MEL), a nonsteroidal anti-inflammatory drug was chosen as a poorly water-soluble model drug and formulated in order to enhance its dissolution using solvent-based electrospinning. Three polyvinylpyrrolidone (PVP) derivatives (K30, K90 and VA 64), Soluplus and (2-Hydroxypropyl)-β-cyclodextrin were used to create five different amorphous solid dispersions of meloxicam. Through experimental design, the various formulation additives that were believed to influence the characteristics of dissolution and permeation through an artificial membrane were observed by carrying out a simultaneous dissolution-permeation study as further described below.

Figure 12:
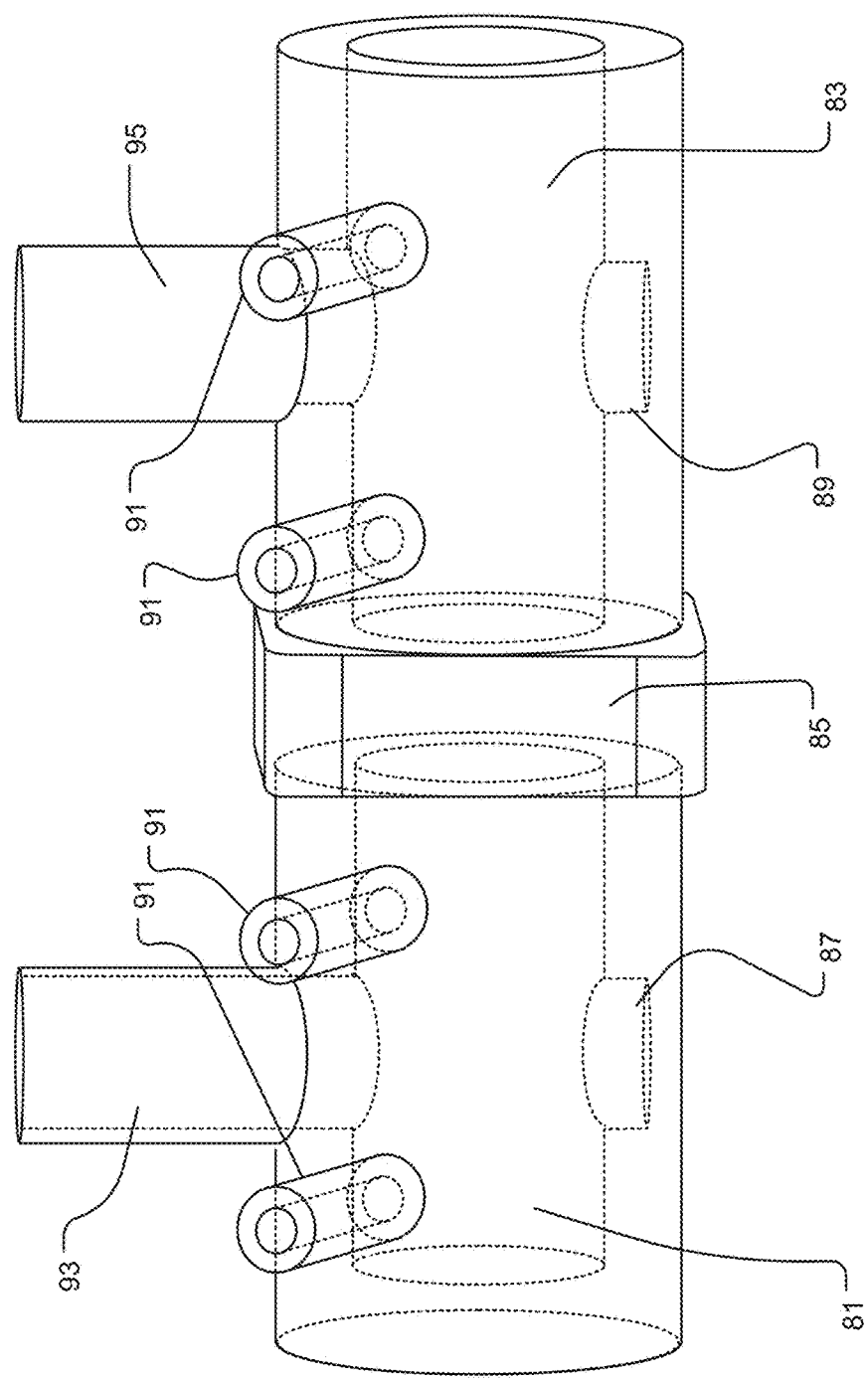
FIG. 12 is a diagram showing an apparatus suitable for conducting in vitro dissolution-permeation studies.

The in vitro dissolution-absorption studies were carried out using a µFLUX™ (Pion Inc., Billerica Mass., U.S.A.), a schematic diagram of which is shown in FIG. 12. The apparatus included a donor and an acceptor chamber (20 mL volume) separated by an artificial membrane (PVDF, polyvinylidenefluoride, 0.45 µm, 1.54 cm$^2$). In the case of oral drug delivery, the donor chamber represents the gastrointestinal tract, while the acceptor chamber represents the blood circulation. At first 25 µL of gastrointestinal track (GIT) lipid was dribbled on the membrane surface, then 20 mL of pH 6.8 phosphate buffer was added into the donor chamber, and 20 mL of sink buffer was added into the acceptor chamber. The solubility of MEL is 267 mg/L in the acceptor buffer, which meets the requirement for sink condition, i.e. the volume of medium in the acceptor chamber is at least three times greater than required to form a saturated solution of the drug substance. Samples, formulations or DMSO stock (5 mg/ml) equivalent to API load 62 µg/ml, 104 µg/ml and 134 µg/ml were placed in the donor chamber. Both chambers were stirred at 150 rpm at 37° C. In both chambers the API concentration was followed by immersed UV-probes at 363 nm using the Rainbow Dynamic Dissolution Monitor System® (Pion Inc., Billerica, Mass., U.S.A.).

The flux across the membrane was calculated using the following equation:

$$J(t) = \frac{\Delta n}{A * \Delta t}$$

where the flux (J) of a drug through the membrane is defined as the amount (n) of drug crossing a unit area (A) perpendicular to its flow per unit time (t).

Figure 14A:
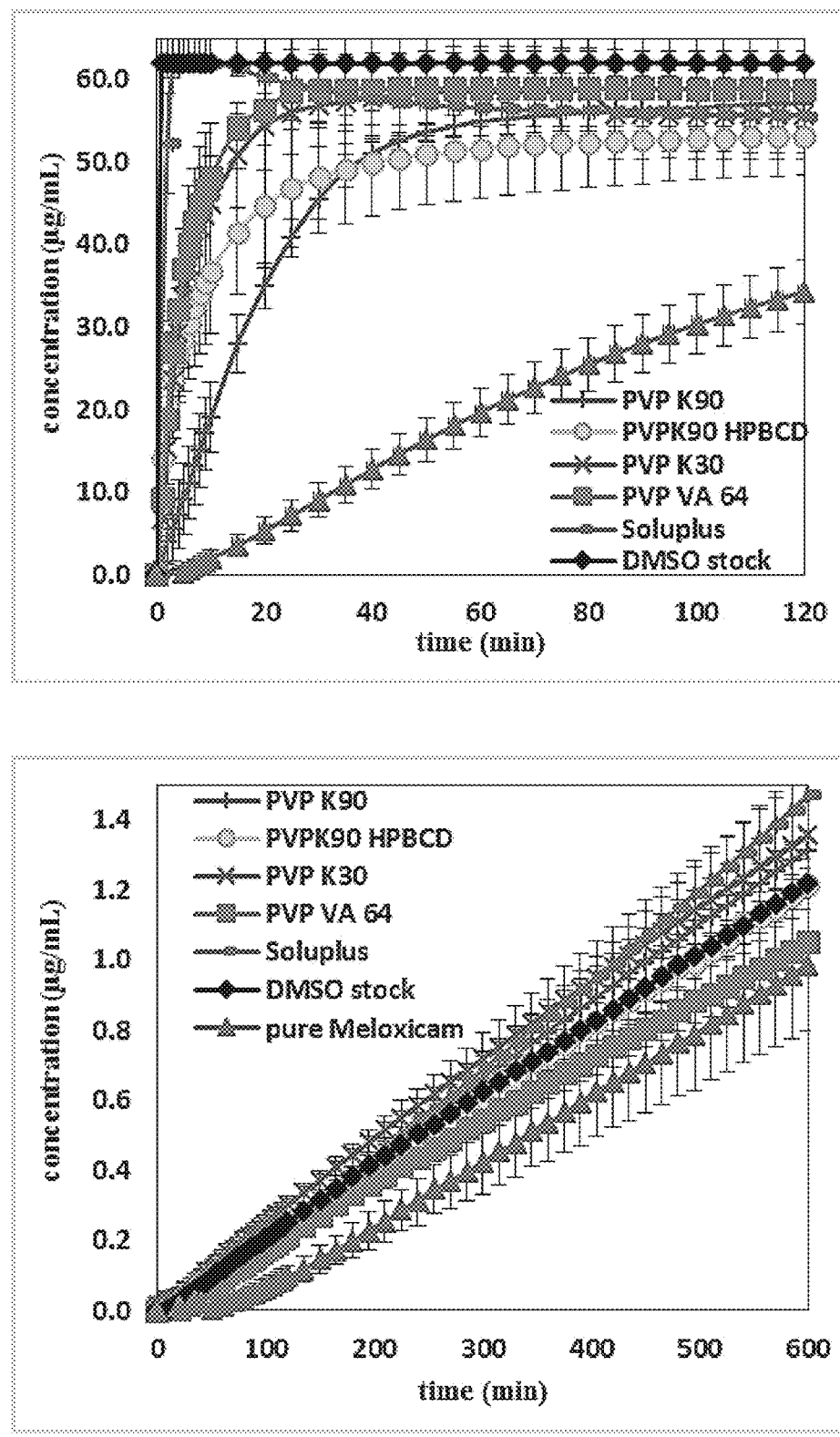
FIGS. 14A through 14C present time dependent data for API concentrations in the donor compartment and the acceptor compartment of the apparatus in FIG. 12 for different meloxicam (MEL) formulations at three different loadings: A 62 μg/mL; B 104 μg/mL; and C 134 μg/mL.
Figure 14B:
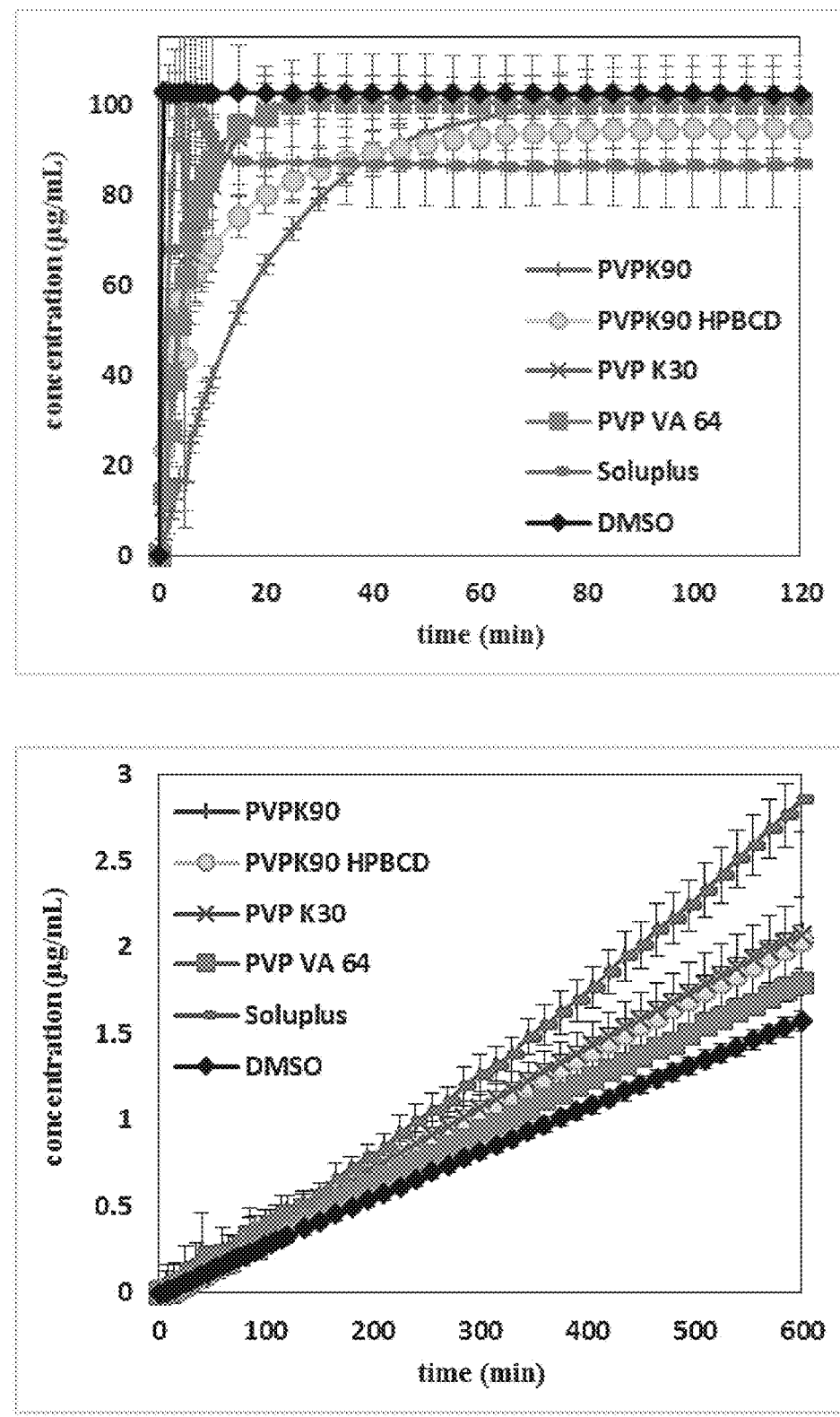
Figure 14C:
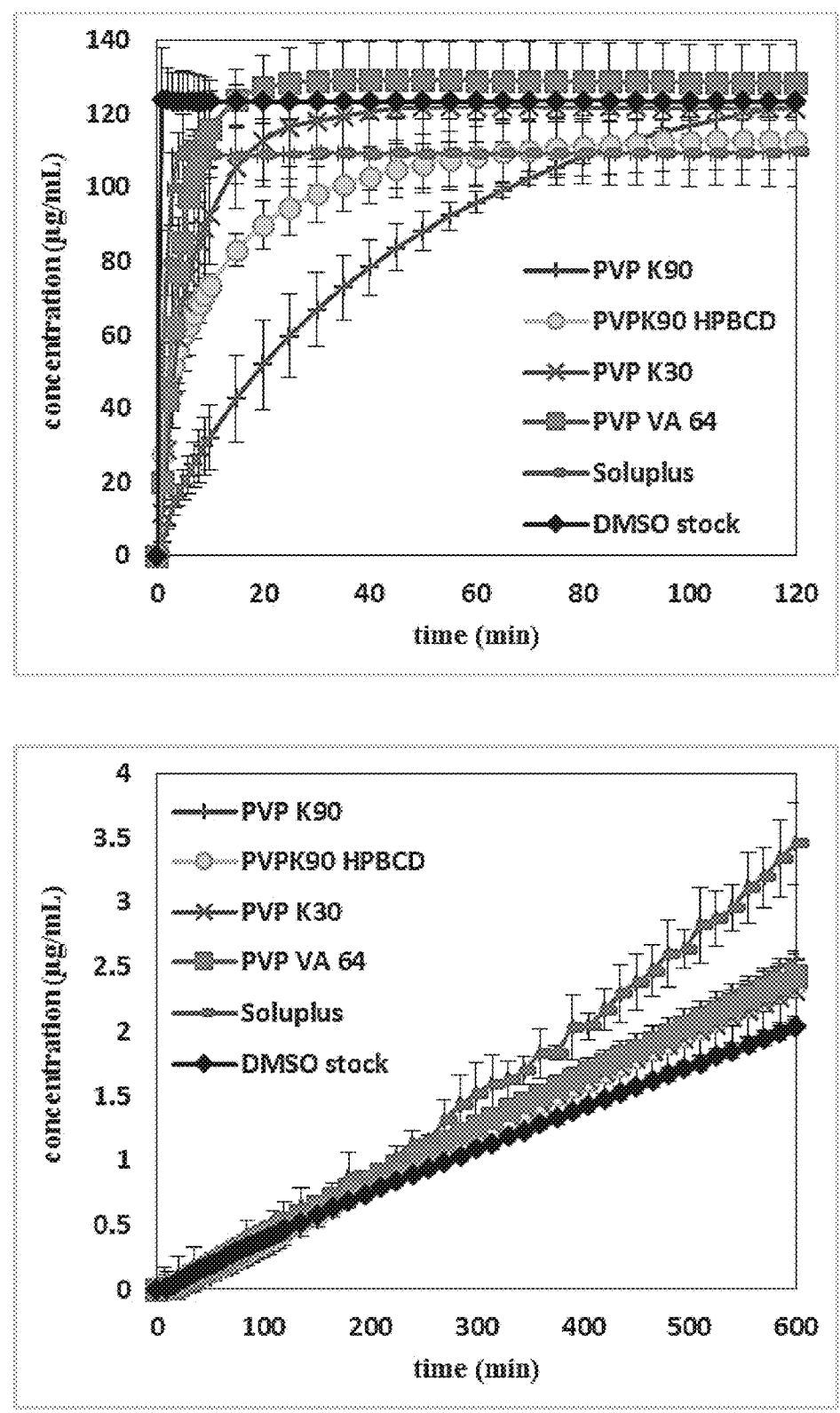

FIGS. 14A, 14B and 14C show API concentration in the donor compartment and the acceptor compartment for API loads of 62 µg/mL, 104 µg/mL, and 134 µg/mL, respectively, 0.05 mol/dm$^3$ KH$_2$PO$_4$ buffer in the donor compartment, GIT membrane, sink buffer as acceptor (ASB), 150 rpm, 37° C. The dissolution profiles in the donor chambers showed that from all formulations the dissolved amount of drug was over 90% in the case of 62 µg/mL, 104 µg/mL and 134 µg/mL loads, demonstrating a significant improvement compared to the crystalline API. Among the five dissolution profiles of electrospun formulations only slight differences were observed. From the Soluplus and PVP VA 64 containing formulations the drug dissolved slightly faster than from HP-β-CD containing formulation. In the case of 62 µg/mL load, the solutions in the donor chambers were slightly subsaturated. While the dissolution of the API from all formulations improved by more than 100% compared to the crystalline MEL, the flux through the membrane did not change significantly among formulations, except for the Soluplus containing formulation. This can be explained by the fact that, in contrast with other formulation additives which do not alter solubility, Soluplus decreased the solubility of MEL, leading to supersaturated solution in the donor chamber even in case of 62 µg/mL dose. These results indicate that supersaturated solutions can have superior thermodynamic activity compared to subsaturated solution with the same concentration.

Applying 104 µg/mL or 134 µg/mL loads in the donor chamber generated supersaturated solutions from all formulations. The flux through the membrane in case of Soluplus containing formulation was nearly twice as much as from formulations made of PVP derivatives, which is in agreement with the degree of supersaturation created in donor chambers from different formulations.

However, based on the solubility results only subsaturated solutions are formed from DMSO stock solutions and the flux from these solution were just slightly lower than the flux observed with PVP containing supersaturated solutions.

In summary, although the dissolution profiles of the formulations were found to be very similar, in the case of Soluplus containing formulation the flux was superior. Further investigation of the Soluplus containing formulation showed that this flux enhancer effect can be mathematically described by considering the degree of supersaturation (defined as the ratio of dissolved amount of the drug to its thermodynamic solubility) to be the driving force for membrane transport rather than the total concentration gradient.

Example 7

The goal of the study was to develop a method enabling simultaneous monitoring of dissolution of the drug product in a compendial apparatus such as that shown in FIG. 5, for example, while providing, at the same time, the means to assess the kinetics of API penetration into the absorption chamber separated from the dissolution vessel by a lipophilic membrane.

The apparatus, which included a receiver chamber integrated with permeation membrane, an overhead stirrer and fiber optic (FO) UV probe was inserted in a standard 900 mL vessel of USP II apparatus. A filter-supported artificial membrane (Double-Sink™ PAMPA (see, for example, A. Avdeef, O. Tsinman, *PAMPA—A Drug Absorption In Vitro Model. 13. Chemical Selectivity Due to Membrane Hydrogen Bonding: In Combo Comparisons of HDM-, DOPC-, and DS-PAMPA Models*, Eur. J. Pharm Sci. 2006, 28 (1), 43-59, incorporated herein by reference in its entirety) with 3.8 cm² area separated the dissolution (donor) compartment from the receiver compartment and contained 15 mL of Acceptor Sink Buffer at pH 7.4 (ASB, Pion, Inc.). The integrated fiber-optic UV probes were positioned in the donor and receiver compartments allowing real time concentration monitoring in both chambers.

The drug selected was Naproxen (abbreviated herein as NPX):

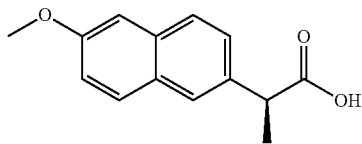 [SMILES: COc1ccc2cc([C@H](C)C(=O)O)ccc2c1]

The formulations used were: (i) over the counter brand name NPX sodium 220 mg dose liquid gel capsules (Alive® Liquid Gels, Bayer); and (ii) a generic supermarket brand of NPX sodium caplets at the same 220 mg dose.

Concentration monitoring in both dissolution and absorption chambers was conducted using fiber optic UV probes connected to a Rainbow Dynamic Dissolution Monitor System® (Pion Inc., Billerica, Mass., U.S.A.).

Flux (J) of a drug through a membrane is defined as the amount of drug crossing a unit area perpendicular to its flow per unit time. In the one-dimension steady-state approximation it may be expressed through the effective permeability coefficient $P_e$ and concentration c(t) in the donor compartment as follows:

$$J(t)=dm/A\cdot dt=P_e\cdot c(t)$$

The experiment began in 800 milliliters (mL) at a pH of 1.6, simulating gastric conditions. After 30 minutes, the medium in the dissolution vessel was converted to the biorelevant dissolution medium FaSSIF (Fasted-State Simulated Intestinal Fluid) by adding 200 mL of specially formulated concentrate.

Figure 15:
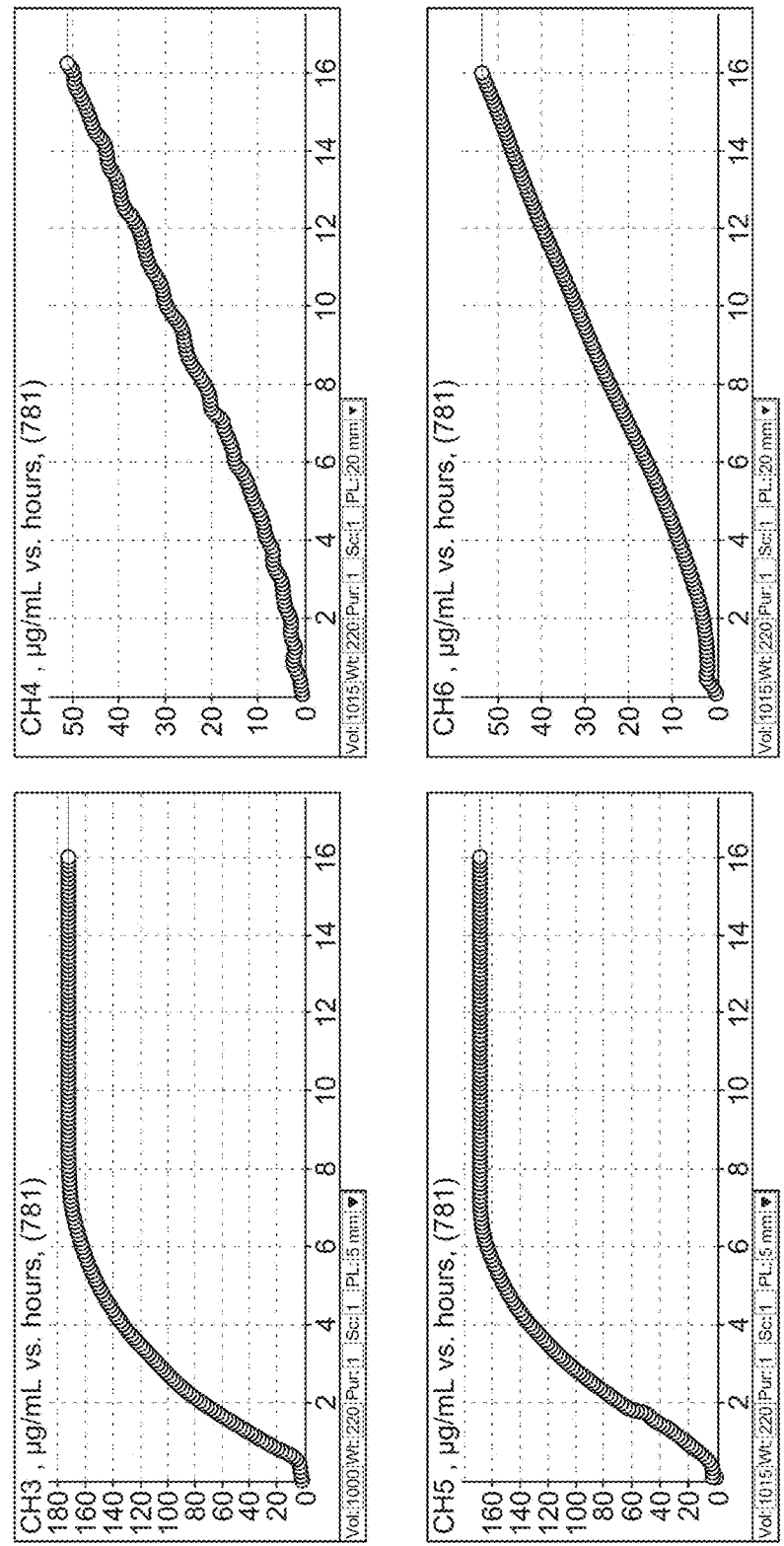
FIGS. 15 and 16 show dissolution (left) and appearance (right) profiles of, respectively, brand and generic naproxen (NPX) formulations measured using the apparatus of FIG. 5.
Figure 16:
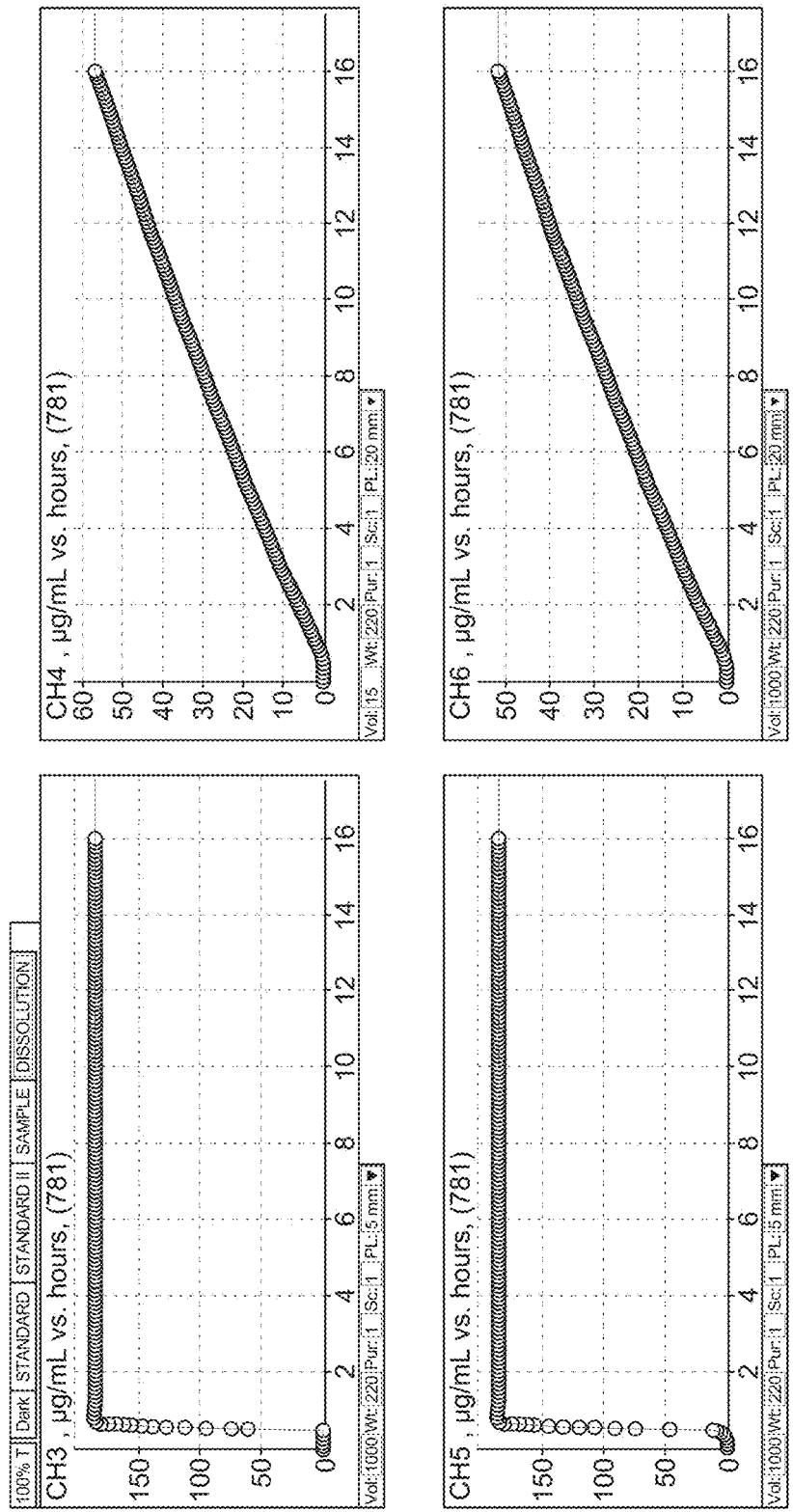
Figure 17A:
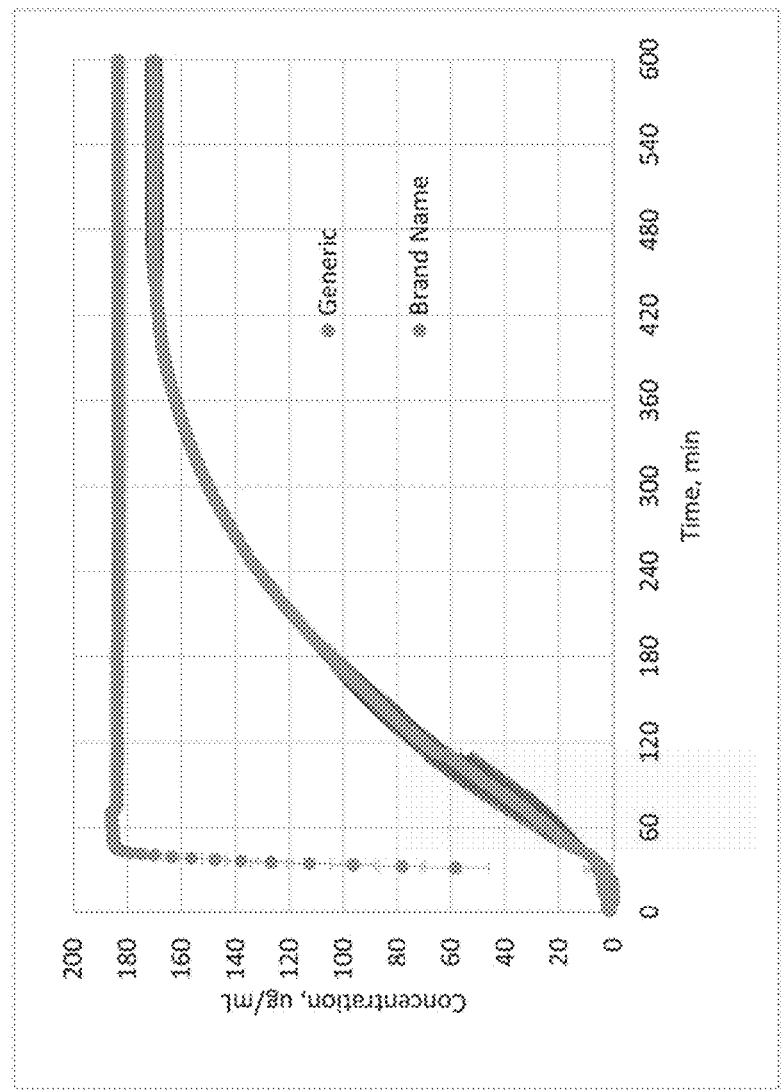
FIG. 17A shows the average dissolution profile of NPX, determined in the apparatus of FIG. 5, with the upper plot reflecting the behavior of the generic formulation (ii) and the lower plot that of the brand name product (i).

FIGS. 15 and 16 show dissolution (left) and appearance (right) profiles of, respectively, brand and generic NPX formulations. The results showed that the brand name and generic NPX products exhibited very different release profiles, with the behavior of the brand formulation (i) being consistent with extended or sustained release profile, while the generic formulation (ii) behaved according to an immediate (fast) release profile. Averaged dissolution profile data (n=3) are shown in FIG. 17A, with the upper curve reflecting the behavior of the generic formulation (ii) and the lower curve corresponding to the brand name (i) product.

It is interesting to note that the generic brand (ii) had no dissolution in Simulated Gastric Fluid (SGF) for the first 20 min and this resulted in no flux being generated during this period of time. In contrast, the brand name product (i) released some NPX in the first 30 min. It is believed that NPX as an acid had highest permeability at the lowest pH value, explaining a quite substantial flux even when concentration of NPX was so low.

Figure 17B:
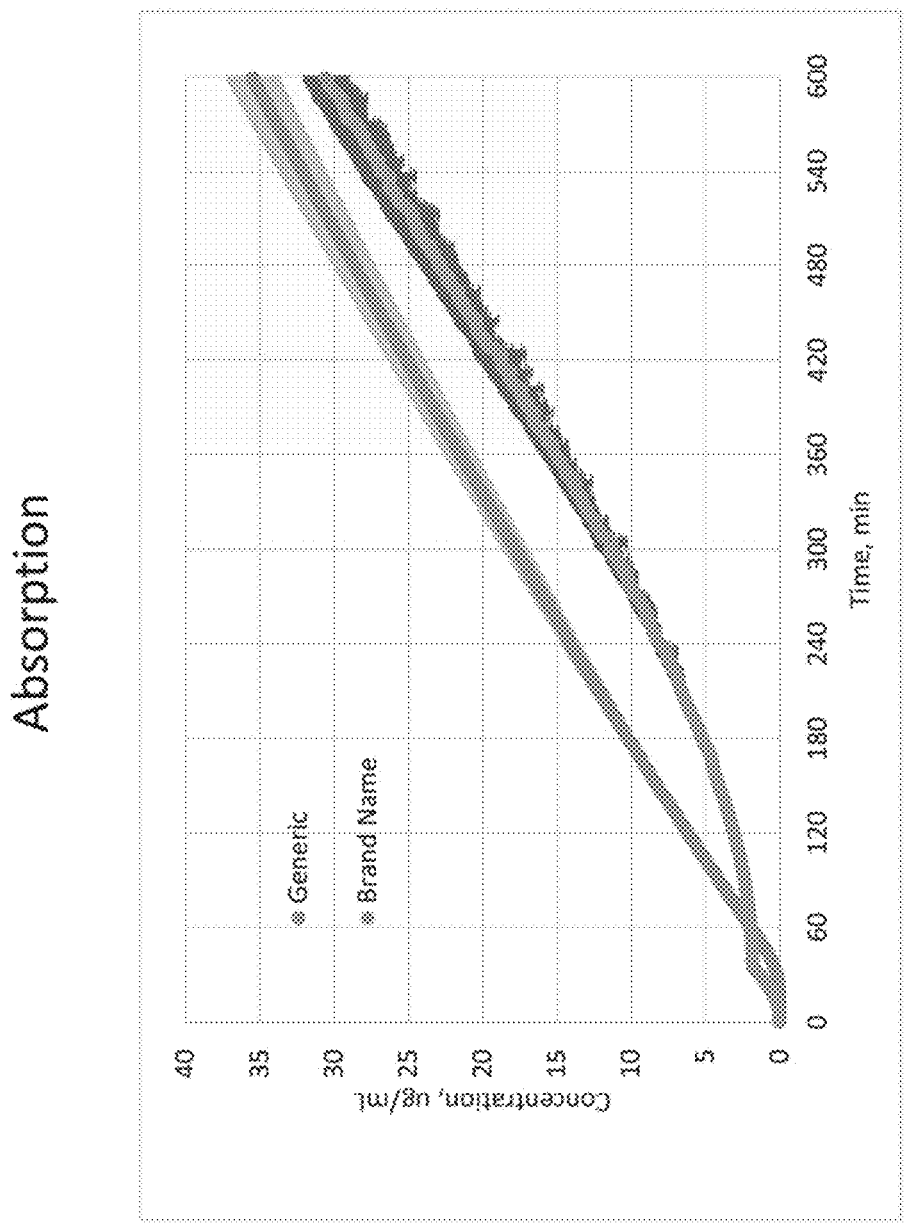
FIG. 17B shows concentration-time profiles of NPX in the receiver vessel of the apparatus of FIG. 5 for the first 10 hours of the experiment, with the upper plot reflecting the behavior of the generic formulation (ii) and the lower plot that of the brand name product (i).

Maximum flux for the generic formulation (ii) established immediately after the SGF-FaSSIF media change and then remained nearly constant for the duration of the experiment, while for the brand name formulation (i) flux reached its maximum value after about 3.5 hours from the media change offset time (see FIG. 17B, brand name formulation (i), lower curve; generic formulation (ii), upper curve), showing the concentration-time profile of NPX in the receiver compartment for the first 10 hours of the experiment.

Table 4 shows NPX flux values ($\mu g/(cm^2 \cdot min)$) for different time segments (in minutes) of the assay:

TABLE 4

| Formulation | 20-30 min | 40-100 min | 200-600 min |
| --- | --- | --- | --- |
| Flux - Brand Nam (i) | 0.30 (0.04) | 0.05 (0.01) | 0.25 (0.01) |
| Flux - Generic (ii) | <0.01 | 0.29 (0.02) | 0.24 (0.02) |

The setup used in these experiments allowed combining conventional dissolution studies with investigation of permeation of the released compound into the absorption chamber. The investigation demonstrated good reproducibility of results for both dissolution (donor) and receiver chambers. With acceptor sink buffer (ASB) being used in the receiver chamber it was possible to maintain sink conditions for the studied API despite the limited volume (15 mL) of the compartment.

It is believed that the device can become an alternative platform to the bi-phasic dissolution method (see, e.g., D. M. Mudie, Y. Shi, H. Ping, P. Gao, G. L. Amidon, G. E. Amidon, *Mechanistic Analysis of Solute Transport in an In Vitro Physiological Two-Phase Dissolution Apparatus*, Biopharm. Drug Dispos. 2012 33, 378-402) for In Vivo Predictive Dissolution (IPD) studies.

As used herein, the term "and/or" includes any and all combinations of one or more of the associated listed items. Further, the singular forms of the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for assessing an in vivo absorption of a compound or a compound product, the method comprising:
    introducing the compound or the compound product into a first or a dissolution medium;

allowing dissolved compound or compound product to transfer from the first or the dissolution medium to a second or a receiving medium through a permeation membrane separating the first or the dissolution medium and the second or the receiving medium;

measuring the amount of dissolved compound or compound product in the second or the receiving medium as a function of time to determine an absorption potential parameter; and (i) measuring the amount of dissolved compound or compound product in the first or the dissolution medium as a function of time to obtain a concentration profile or a dissolution rate;

monitoring for a change in the concentration profile or in the dissolution rate; and comparing the change or a lack thereof in the concentration profile or the dissolution rate in the first or the dissolution medium with a change or lack thereof in the absorption potential parameter, or (ii) measuring the amount of dissolved compound or compound product in the first or the dissolution medium as a function of time to obtain a concentration profile or a dissolution rate;

monitoring for a change in the absorption potential parameter; and comparing the change or a lack thereof in the absorption potential parameter with a change or lack thereof in the concentration profile or the dissolution rate in the first or the dissolution medium, wherein the second or the receiving medium is contained in a receiving vessel that is partially or completely immersed in the first or the dissolution medium.

2. The method of claim 1, wherein the first or dissolution medium is contained in a dissolution vessel that includes a basket or a paddle.

3. The method of claim 2, wherein the dissolution vessel has a volume of 250 mL, 500 mL or 900 mL.

4. The method of claim 1, wherein the first or the dissolution medium is a model for an in vivo medium on a donor side of an in vivo membrane and/or the second or the receiving medium is a model for an in vivo medium on an acceptor side of the in vivo membrane.

5. The method of claim 1, further comprising expressing the absorption potential parameter as a flux of the compound or compound product through the permeation membrane, wherein the flux is the amount of the compound or compound product penetrating through the membrane ver unit area ver unit time.

6. The method of claim 1, further comprising stirring at least one of the first or the dissolution medium and the second or the receiving medium.

7. The method of claim 1, wherein the compound or the compound product is provided as a loose powder, a compacted powder, a liquid formulation, a viscous formulation, a patch formulation or a sublingual strip formulation or wherein the compound is a pharmaceutically active ingredient, a veterinary, toxic or a hazardous substance, a dietary supplement, or a recreational drug.

8. The method of claim 1, further comprising measuring the amount of dissolved compound or compound product in the first or the dissolution medium, the amount of dissolved compound or compound product in the second or the receiving medium or the amount of dissolved compound or compound product in both media by a spectroscopic or potentiometric technique in situ, or on a continuous basis, or by withdrawing aliquots.

9. The method of claim 1, wherein the membrane is or mimics an in-vivo membrane.

10. The method of claim 1, wherein the membrane is selected from the group consisting of a PAMPA type membrane-, a cell mono or multi-layer, a skin or skin-like membrane, a dialysis membrane, a mucosal membrane, an ocular membrane, and a corneal membrane.

11. The method of claim 1, wherein the volume occupied by the second or the receiving medium is smaller than the volume occupied by the first or the dissolution medium, or wherein the first or the dissolution medium is a donor medium and the second medium is a receiving medium.

12. The method of claim 1, further comprising comparing amounts of compound or compound product or dissolved compound or compound product determined as a function of time in the first or the dissolution medium, in the second or the receiving medium or both with calibration curves to determine the BCS class of the compound, or the method of claim 1, further comprising computerized data collection and/or analysis.

13. A method for assessing effects of permeation on a dissolution rate of a compound, the method comprising:

introducing the compound into a dissolution medium;

allowing the compound to permeate through a semipermeable membrane to a receiving medium;

measuring a first concentration of the compound in the dissolution medium as a function of time to obtain a first concentration profile in the presence of permeation of the compound to the receiving medium; and comparing the first concentration profile with a second concentration profile of the compound in the dissolution medium, wherein the second concentration profile is obtained in the absence of permeation to the receiving medium, to determine which parameter from the group consisting of dissolution rate, solubility and permeability is a limiting factor for absorption of the compound, wherein the semipermeable membrane separates the dissolution medium and the receiving medium, and wherein the receiving medium is contained in a vessel that is partially or completely immersed in the dissolution medium.

14. The method of claim 13, further comprising:

measuring amounts of the compound or dissolved compound as a function of time and in the presence of permeation in the dissolution medium, in the receiving medium or both; and comparing the measured amounts of the compound or dissolved compound determined as a function of time in the dissolution medium, in the receiving medium or both, with calibration cures to determine the BCS class of the compound.

15. The method of claim 13, wherein the semipermeable membrane is selected from the group consisting of a PAMPA type membrane, a cell mono or multi-layer, a skin or skin-like membrane, a dialysis membrane, a mucosal membrane, an ocular membrane and a corneal membrane.

16. The method of claim 13, wherein the compound is provided as a loose powder, a compacted powder, a liquid formulation, a viscous formulation, a patch formulation or a sublingual strip formulation or wherein the compound is a pharmaceutically active ingredient, a veterinary, toxic or a hazardous substance, a dietary supplement, or a recreational drug.

17. The method of claim 13, further comprising measuring the first concentration of the compound by a spectroscopic or potentiometric technique conducted in situ, or on a continuous basis, or by withdrawing aliquots.

* * * * *

UNITED STATES PATENT AND TRADEMARK OFFICE
CERTIFICATE OF CORRECTION

PATENT NO. : 10,228,358 B2
APPLICATION NO. : 15/098514
DATED : March 12, 2019
INVENTOR(S) : Ajit S. Narang et al.

Page 1 of 1

It is certified that error appears in the above-identified patent and that said Letters Patent is hereby corrected as shown below:

In the Claims

In Claim 5, Column 23, Line 48, delete "ver" and insert --per--;

In Claim 5, Column 23, Line 49, delete "ver" and insert --per--;

In Claim 14, Column 24, Line 52, delete "cures" and insert --curves--.

Signed and Sealed this
Twenty-first Day of May, 2019

Andrei Iancu
*Director of the United States Patent and Trademark Office*